United States Patent
Vidal-Vanaclocha

(10) Patent No.: US 10,724,038 B1
(45) Date of Patent: Jul. 28, 2020

(54) TARGET-ORIENTED THERAPEUTIC DRUG AND IN-VITRO METHOD OF DISCOVERY THEREOF FOR MODULATING ONSET OR PROGRESSION OF LIVER METASTASIS

(71) Applicant: Persona Biomed, Inc., Alexandria, VA (US)

(72) Inventor: Fernando Vidal-Vanaclocha, Alexandria, MD (US)

(73) Assignee: Persona Biomed, Inc., Alexandria, VA (US)

( * ) Notice: Subject to any disclaimer, the term of this patent is extended or adjusted under 35 U.S.C. 154(b) by 0 days.

(21) Appl. No.: 16/213,905

(22) Filed: Dec. 7, 2018

Related U.S. Application Data

(60) Provisional application No. 62/596,872, filed on Dec. 10, 2017.

(51) Int. Cl.
| | |
|---|---|
| *A61K 48/00* | (2006.01) |
| *C07H 21/02* | (2006.01) |
| *C12N 15/113* | (2010.01) |
| *C12Q 1/6886* | (2018.01) |

(52) U.S. Cl.
CPC ........ *C12N 15/113* (2013.01); *C12N 15/1136* (2013.01); *C12N 15/1137* (2013.01); *C12N 15/1138* (2013.01); *C12Q 1/6886* (2013.01); *C12N 2310/111* (2013.01); *C12Q 2600/106* (2013.01)

(58) Field of Classification Search
CPC ................................................ C12N 2310/14
See application file for complete search history.

(56) References Cited

U.S. PATENT DOCUMENTS

2002/0037280 A1* 3/2002 Lieber .................... C12N 15/86
424/93.21

FOREIGN PATENT DOCUMENTS

| WO | WO 98/55618 | * 12/1998 | ........... A61K 31/713 |
|---|---|---|---|
| WO | WO 2008/109354 A1 | * 9/2008 | ........... A61K 31/713 |
| WO | WO 2014/198817 A1 | * 12/2014 | ........... A61K 31/713 |

OTHER PUBLICATIONS

Petrilli et al. (Curr Opin Oncol. Jan. 2017;29(1):35-40).*
Kucharzik et al. (Clin Exp Immunol, 1997, 110, 296-302).*
Benedicto et al. (Oncology Letters, 14, 3883-3892, Oct. 2017).*
Qin et al. (Journal of Translational Medicine, 2013, 11:70, pp. 1-10).*
Wilson et al. (Cancer Res, 2010, 70(2), 609-620).*
Przbyla et al. (Acta Biochim Pol. 2017;64(2):315-322).*
Nikiteas et al. (World J Gastroenterol. Mar. 21, 2005;11(11):1639-43).*
Meihua et al. (Int J Oncol. Feb. 2004;24(2):305-12).*
Vellinga et al. (Ann Surg. Nov. 2017;266(5):765-771).*
Dong et al. (Mod Pathol. Jan. 2009;22(1):151-60), T.*
Tang et al. (J Bioenerg Biomembr. Feb. 2012;44(1):117-25).*
Zhang et al. (Int J CLin Exp Med, 2015, 8(9), 15900-15909).*

* cited by examiner

*Primary Examiner* — Amy H Bowman
(74) *Attorney, Agent, or Firm* — Harbin & Hein PLLC

(57) ABSTRACT

An in vitro method to discover or screen various an agent capable of modulating onset or progression of hepatic metastasis through inhibition or suppression of genes associated with prometastatic reaction in hepatic tissue. The method comprises preparing a primary mix-culture of hepatic parenchymal and non-parenchymal cells, exposing cells to colorectal cancer cells to induce a prometastatic reaction; the exposing the cells to the therapeutic agent to be screened, and then measuring gene expression profiles of cells exposed to the agent, and finally comparing the measured gene expression profile to a reference gene expression profile whereby to determine if the agent has a positive effect on inhibiting or suppressing metastatic reaction. Also disclosed is an array of compositions to identify an agent comprising an antisense oligonucleotide capable of treating a colorectal cancer patient each having a nucleotide sequence that hybridizes with group 1 genes (PRDX4, CRP, ID1, MT1E, TNFSF14, MRC1, ICAM1, IL18, IL10, TFN) and/or group 2 genes (NGF, EPHA1, ERBB2IP, SDC1, COL18A1, KNG1, ADH1B, CYP2E1).

6 Claims, 32 Drawing Sheets

US 10,724,038 B1

TARGET-ORIENTED THERAPEUTIC DRUG AND IN-VITRO METHOD OF DISCOVERY THEREOF FOR MODULATING ONSET OR PROGRESSION OF LIVER METASTASIS

CROSS REFERENCE TO RELATED APPLICATION

This invention claims the benefit of U.S. Provisional Application Ser. No. 62/596,872 filed Dec. 10, 2017 in the name of the same inventor hereof and entitled Target-Oriented Therapeutic Drug and In-Vitro Method of Discovery Thereof for Modulating Onset or Progression of Liver Metastasis, which is incorporated herein.

BACKGROUND

This invention concerns a method of drug discovery and resulting therapeutic agent for treating a patient with metastatic cancer in the liver stemming from a primary colorectal cancer or digestive tract disorder.

The inventor hereof has discovered that development of hepatic metastases is associated with an aberrant tissue-reconstitution process that results from bidirectional reciprocal effects between cancer cells and resident hepatic cells. On one hand, cancer cells and their soluble and exosomal proteins regulate gene expression in hepatic cells residing in, or infiltrating into, various sites of metastases. At these sites, cancer cells exert selective pressures on hepatic cells thereby shaping their functional phenotypes. Conversely, constituents of the liver microenvironment may also regulate gene expression in the cancer cells thereby controlling their fate and determining their ability to progress towards metastatic formation (for review, see Vidal-Vanaclocha, 2011a).

Additionally, there are pathophysiological processes such as aberrant hepatic regeneration, inflammation and fibrosis that change the hepatic microenvironment and notably affect development of metastases. Therefore, tumor microenvironment regulating hepatic metastasis in a given patient consists of structural and functional factors resulting from both hepatic-cancer cell interactions and previous or concurrent hepatic diseases (for review, see Vidal-Vanaclocha, 2011b).

Neoplasms from right and left colon and rectum frequently metastasize to the liver. At a transcriptional level, hepatic metastasis development is in part associated with marked changes in gene expression of colorectal cancer cells that may originate in a primary tumor. Other prometastatic changes occur in the liver and are regulated by hepatic cells, which represent a new microenvironment for metastatic colon cancer cells. In addition, hepatic parenchymal and non-parenchymal cell functions are also affected by both cancer cell-derived factors and various systemic pathophysiological factors of a patient having CRC.

Liver and gastrointestinal tract physiology and pathology are interrelating, For example, gallstones (cholelithiasis) and cholecystectomy are related to digestive system cancer through inflammation, altered bile flux, and changes in metabolic hormone levels. More importantly, it has been established that a statistically significant risk of colorectal cancer follows cholelithiasis (Lee et al, 2016; Gosavi et al, 2017). Similarly, fatty liver, which is a hepatic manifestation of metabolic syndrome, is a well-known risk factor for CRC (Barbois et al, 2017). If hepatic gene expression disorders precede CRC occurrence, early biomarkers of CRC risk and development may be assessed.

In the past two decades, a growing amount of data has been reported suggesting that carcinomas of the right and left colon should be considered as different tumor entities. Right-sided colon cancers (RCC) and left-sided colon cancers (LCC) are of different embryological origins, and various differences exist between them. Tumor location is associated with prognosis in colorectal cancer patients, and those with RCC have a significantly worse prognosis than those with LCC (Yahigi et al 2016). RCC should be treated distinctively from LCC (Zhao et al, 2017), and the establishment of standardized management for colon cancer by tumor location is needed.

Characterization of genes that are differentially expressed in tumorigenesis is an important step in identifying those that are intimately involved in the details of a cell's transformation from normal to cancerous, and from non-metastatic to metastatic cells, However, little is known about molecular changes that occur in key organs (as for example the liver) during the course of cancer development and its metastatic disease. While changes in the expression level of individual genes have been reported, investigation of gene expression changes that occur in the liver of patients with cancer and without cancer as provided by the present invention has not been previously known or documented.

In brief summary, there exists a need in the art for the identification of new CRC disease-associated hepatic genes as molecular biomarkers to, among other things, (i) monitor and assess the pathogenic contribution of liver to CRC and hepatic CRC metastasis development; (ii) identify and/or screen candidate cancer patients suitable for liver metastasis-specific therapies; and (iii) discover and/or screen pharmaceutical cellular and molecular compositions targeting those liver genes with CRC and CRC metastasis-stimulating activities in patients with and without colorectal cancer.

These and other needs are met by various aspects of the present invention.

SUMMARY

In accordance with a first aspect of the invention, there is provided an in vitro method of screening an agent potentially capable of modulating onset or progression of hepatic metastasis through inhibition or suppression of selected group 1 genes associated with prometastatic reaction in hepatic tissue, where the selected group 1 genes comprises a combination of a majority of genes selected from the group (PRDX4, CRP, ID1, MT1E, TNFSF14, MRC1, ICAM1, IL18, IL10, TNF), and where the method comprises (a) preparing a primary mix-culture of hepatic parenchymal and non-parenchymal cells obtained form a target patent; (b) exposing the primary mix-culture of hepatic parenchymal and non-parenchymal cells to colorectal cancer (CRC) cell-derived soluble factors to induce a prometastatic reaction in vitro; (c) after said exposing of step (b), generating a set of reference levels indicative of gene expression levels of the selected group 1 genes of the hepatic parenchymal and non-parenchymal cells of the primary mix culture; (d) exposing the primary mix-culture of hepatic parenchymal and non-parenchymal cells to the agent; (e) after said exposing step (d), measuring gene expression levels of each of said selected group 1 genes of the hepatic parenchymal and non-parenchymal cells of said mix culture that were exposed to said agent; and (f) respectively comparing measured gene expression levels of each of the levels generated in step (c) whereby to determine if the agent has a positive effect on inhibiting or suppressing activity of group 1 genes associated with metastatic reaction.

The hepatic parenchymal cells of the primary mix culture may comprise hepatocytes and the non-parenchymal cells may comprise sinusoidal and non-sinusoidal stromal cells from human or mouse livers.

After said first exposing step (b), validating the method may include obtaining a relationship where the selected group 1 genes in the mix culture are relatively overexpressed, selected group 2 genes in the mix culture are relatively underexpressed, and selected group 3 genes in the mix culture are neither overexpressed or underexpressed where selected group 2 genes comprise a majority of genes (NGF, EPHA1, ERBB2IP, SDC1, COL18A1, KNG1, ADH1B, CYP2E1) and selected group 3 genes comprise a majority of genes (HP, VTN, RPS27, RPL23, GAPDH, TXN, VEGFA, CEACAM1, IGF1, TFGB1, DDR2, NOS2, and BMP7).

In yet another aspect of the invention, agents may comprise one or more of a pharmaceutical cellular and molecular composition, target-oriented natural product or synthetic chemical analog thereof, a small or large molecule drug or organic compound, and a drug conjugate including but not limited to nanoconjugates and/or polymer-based combinations thereof.

A further aspect of the invention includes colorectal cancer cell-derived soluble factors of step (b) comprising human or mouse-derived cells.

An additional aspect of the invention includes (i) hepatic parenchymal and non-parenchymal cells being obtained from a target patent with colorectal cancer, (ii) selected group 1 genes comprising all genes (PRDX4, CRP, ID1, MT1E, TNFSF14, MRC1, ICAM1, IL18, IL10, TNF), (iii) selected group 2 genes comprising all genes (NGF, EPHA1, ERBB2IP, SDC1, COL18A1, KNG1, ADH1B, CYP2E1), and (iv) selected group 3 genes comprising all genes (HP, VTN, RPS27, RPL23, GAPDH, TXN, VEGFA, CEACAM1, IGF1, TFGB1, DDR2, NOS2, and BMP7).

Abbreviated gene designations set forth herein have the following meaning according to the HUGO Gene Nomenclature Committee:

PRDX4, Peroxiredoxin 4
CRP, C-reactive protein
ID1, Inhibitor of DNA binding 1, HLH protein
MT1E, Metallothionein 1E
TNFSF14, TNF superfamily member 14
MRC1, Mannose receptor C-type 1
ICAM1, Intercellular adhesion molecule 1
IL18, Interleukin-18
IL10, Interleukin-10
TNF, Tumor Necrosis Factor alpha
NGF, Nerve growth Factor
EPHA1, EPH receptor A1
ERBB21P, Erbb2 interacting protein
SDC1, Syndecan 1
COL18A1, Collagen type XVIII alpha 1 chain
KNG1, Kininogen 1
ADH1B, Alcohol dehydrogenase 1B (class I), beta polypeptide
CYP2E1, Cytochrome P450 family 2 subfamily E member 1
HP, Haptoglobin
VTN, Vitronectin
RPS27, Ribosomal protein S27
RPL23, Ribosomal protein L23
GAPDH, Glyceraldehyde-3-phosphate dehydrogenase
TXN, Thioredoxin
VEGFA, Vascular endothelial growth factor A
CEACAM1, CEA cell adhesion molecule 1
IGF1, Insulin like growth factor 1
TFGB1, Transforming growth factor beta 1
DDR2, Discoidin domain receptor tyrosine kinase 2
NOS2, Nitric oxide synthase 2
BMP7, Bone morphogenetic protein 7.

These and other aspects of the invention will become apparent upon review of the following description taken in connection with the accompanying drawings. The invention, though, is pointed out with particularity by the appended claims.

BRIEF DESCRIPTION OF THE DRAWINGS

FIG. 1A illustrates hybridization between RNA from metastatic CRC tissue and tumor-unaffected hepatic tissue and FIG. 1B illustrates hybridization between RNA from metastatic CRC tissue and peripheral blood mononuclear cells.

In FIG. 10B, position coordinates of liver prometastatic genes are plotted in correlation circles whose diameters define the influence of genes in the prediction of the class of patient where in this case metabolic bioprotection and fibrogenic/regeneration genes are in the smaller circle indicating that their expression levels had less ability to predict the patient's class than immune protection and proinflammatory genes, mainly located in the large correlation circle, and therefore had a greater predictive capacity to discriminate patients with and without CRC.

Description of Illustrative Embodiments

Disclosed herein are analytical procedures to detect CRC and liver metastasis risk and recurrence and a method to discover drugs suitable for treating candidate patients reasonably with liver metastasis-specific therapies. The invention uses, among other things, a series of mathematical, correlation and statistical analysis techniques to examine, compare and analyze relationships between and among expression levels of uniquely identified genes of hepatic tissues from patients with and without CRC. The invention may include utilization of a data processing device to automate gene analyses presented herein in order to provide a computer-determined output or result for diagnostic and/or treatment guidance to health care practitioners.

Figure 1A:
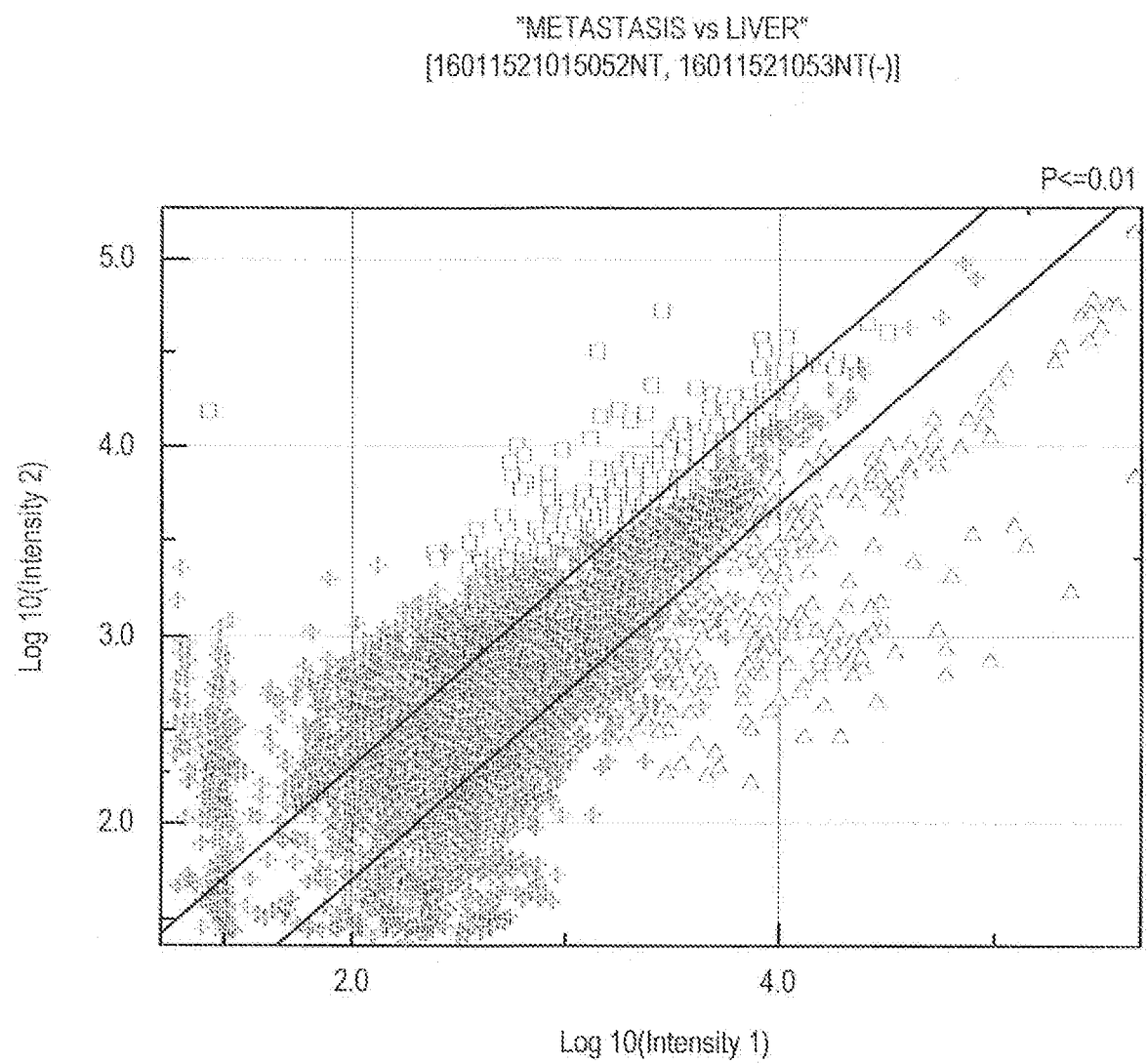
FIGS. 1A and 1B show comparative transcriptomic analysis among metastatic CRC tissue, tumor-unaffected hepatic tissue and peripheral blood mononuclear cells from stage IV patients with CRC having systemic metastasis disease where
Figure 1B:
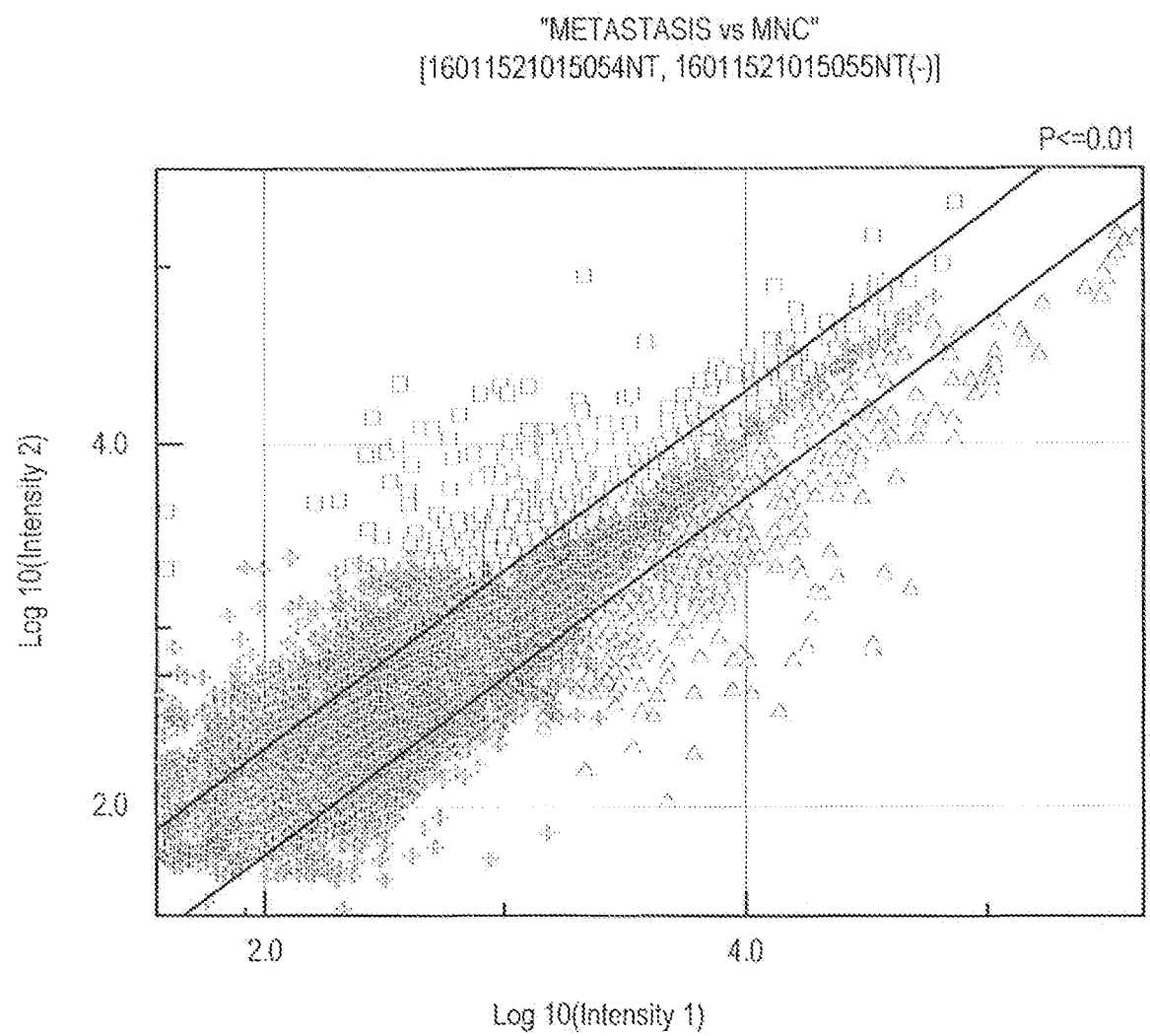
Figures 1C, 1D:
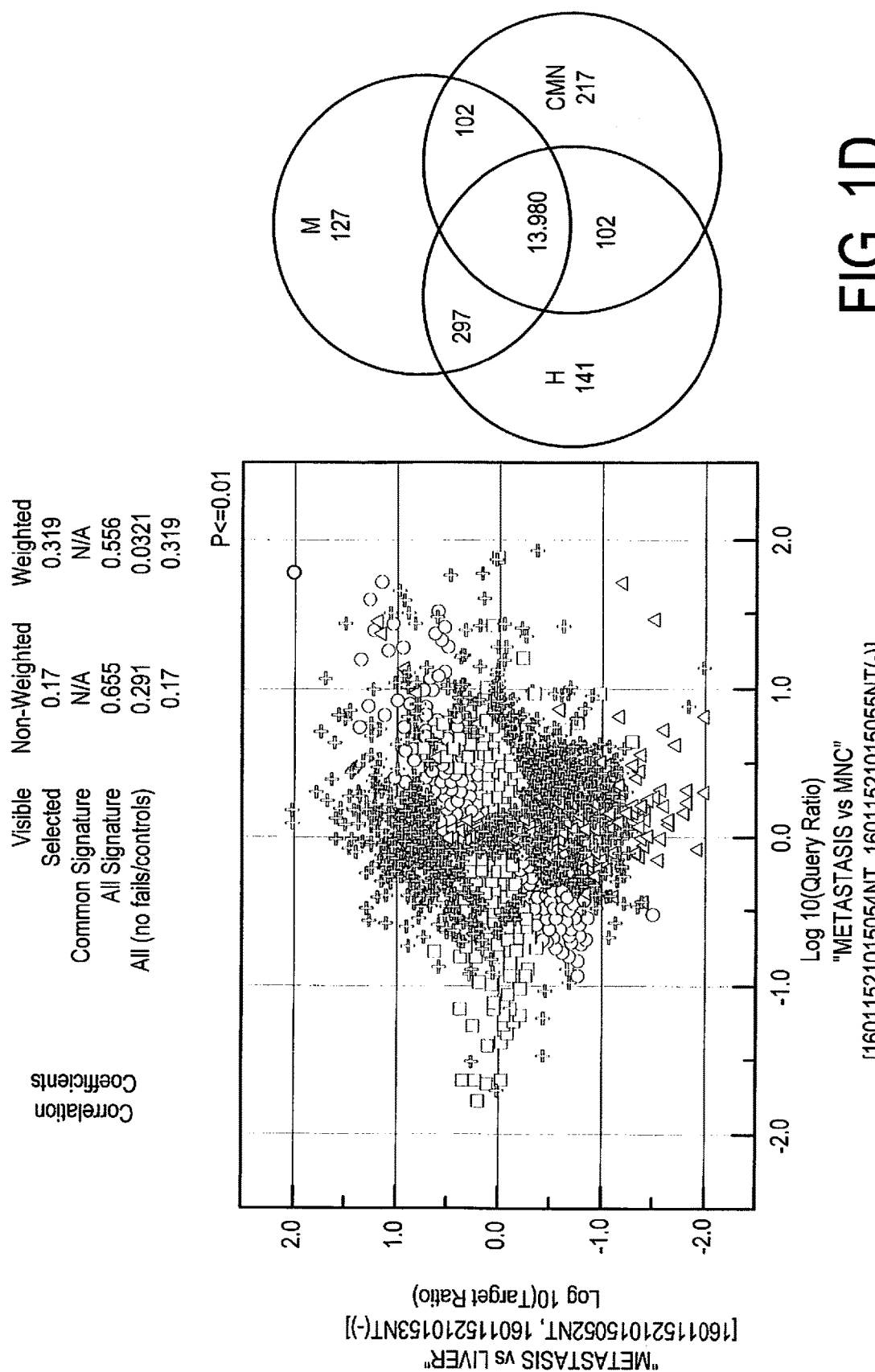
FIG. 1C shows a combination of FIGS. 1A and 1B in a single analysis diagram.
FIG. 1D is a Venn diagram showing overlapping sets of the number of genes for each of the three samples where CMN indicates mononuclear cells, M represent metastatic cells, and H represents tumor unaffected hepatic tissue.

FIG. 1A shows a comparative transcriptomic analysis between metastatic CRC tissue and tumor-unaffected hepatic tissue from Stage N patients with CRC having systemic metastasis disease. FIG. 1B shows a comparative transcriptomic analysis between metastatic CRC tissue and peripheral blood mononuclear cells from Stage N patients with CRC having systemic metastasis disease. FIG. 1C combines that results of FIGS. 1A and 1B, while FIG. 1D shows the data in set and subset relation.

More specifically, FIG. 1A shows hybridization between RNA from Metastatic CRC tissue and tumor-unaffected hepatic tissue; FIG. 1B shows hybridization between RNA from Metastatic CRC tissue and peripheral blood mononuclear cells; FIG. 10 shows a combination of FIGS. 1A and 1B; and FIG. 1D shows the number of genes for each sample compared and illustrated using a Venn diagram where "H" represents hepatic tissue, "M" represents metastatic tissue, and "CMN" represents mononuclear blood cells.

According to the analysis described in connection with FIGS. 1A, 1B, 10 and 1D, Table 1 below lists 122 genes whose expression levels were more than two-fold-upregulated in tumor-unaffected hepatic tissue compared to the expression levels in metastatic tissue and peripheral blood mononuclear cells from Stage N patients with CRC having systemic metastasis disease.

In bold are twenty-one genes whose expression levels were upregulated in liver parenchymal and non-parenchymal sinusoidal cells given the conditioned medium from cultured CRC cells (HT-29 CRC cell line). This gene subset was selected for further analysis.

TABLE 1

| | Upregulated Genes |
|---|---|
| A1BG | Alpha-1-B glycoprotein |
| A2M | Alpha-2-macroglobulin |
| ABAT | 4-aminobutyrate aminotransferase |
| ACAA2 | Acetyl-Coenzyme A acyltransferase |
| ACAT1 | Acetyl-Coenzyme A acetyltransferase 1 (acetoacetyl Coenzyme A thiolase) |
| ADH1A | Alcohol dehydrogenase 1A (class I), alpha polypeptide |
| ADH1B | Alcohol dehydrogenase 1B (class I), beta polypeptide |
| ADH4 | Alcohol dehydrogenase 4 (class II), pi polypeptide |
| AFM | Afamin |
| AGT | Angiotensinogen (serpin peptidase inhibitor, clade A, member 8) |
| AHSG | Alpha-2-HS-glycoprotein (Fetuin A) |
| AKR1C2 | Aldo-keto reductase family 1, member C2 |
| ALAS1 | Aminolevulinate, delta-, synthase 1 |
| ALDOB | Aldolase B, fructose-bisphosphate |
| AMBP | Alpha-1-microglobulin/bikunin precursor |
| ANGPTL4 | Angiopoietin-like 4 |
| AOX1 | Aldehyde oxidase 1 |
| APOA2 | Apolipoprotein A-II |
| APOB | Apolipoprotein B (including Ag(x) antigen) |
| APOC1 | Apolipoprotein C-I |
| APOE | Apolipoprotein E |
| APOH | Apolipoprotein H (beta-2-glycoprotein I) |
| APOM | Apolipoprotein M |
| AQP9 | Aquaporin 9 |
| ARG1 | Arginase, liver |
| ASGR2 | Asialoglycoprotein receptor 2 |
| ATF5 | Activating transcription factor 5 |
| BBC3 | BCL2 binding component 3 |
| BRP44L | Brain protein 44-like |
| C1S | Complement component 1, s subcomponent |
| C3 | Complement component 3 |
| C4A | Complement component 4A (Rodgers blood group) |
| C4BPA | Complement component 4 binding protein, alpha |
| C8A | Complement component 8, alpha polypeptide |
| CBR1 | Carbonyl reductase 1 |
| CFB | Complement factor B |
| CFH | Complement factor H |
| CFHR1 | Complement factor H-related 1 |
| CFHR2 | Complement factor H-related 2 |
| CFI | Complement factor I |
| CLU | Clusterin |
| CP | Ceruloplasmin (ferroxidase) |
| CPS1 | Carbamoyl-phosphate synthetase 1, mitochondrial |
| CRP | C-reactive protein, pentraxin-related |
| CYB5A | Cytochrome b5 type A (microsomal) |
| CYP2C9 | Cytochrome P450, family 2, subfamily C, polypeptide 9 |
| CYP2E1 | Cytochrome P450, family 2, subfamily E, polypeptide 1 |
| CYP3A5 | Cytochrome P450, family 3, subfamily A, polypeptide 5 |
| DDR2 | Discoidin domain receptor tyrosine kinase 2 |
| EPHA1 | EPH receptor A1 |
| ERRFI1 | ERBB receptor feedback inhibitor 1 |
| F11 | Coagulation factor XI (plasma thromboplastin antecedent) |
| F12 | Coagulation factor XII (Hageman factor) |
| F2 | Coagulation factor II (thrombin) |
| F9 | Coagulation factor IX |
| FGA | Fibrinogen alpha chain |
| FGB | Fibrinogen beta chain |
| FGG | Fibrinogen gamma chain |
| FGL1 | Fibrinogen-like 1 |
| FOS | V-fos FBJ murine osteosarcoma viral oncogene homolog |
| FTCD | Formiminotransferase cyclodeaminase |
| GABARAPL3 | GABA(A) receptors associated protein like 3 |
| GAPDH | Glyceraldehyde-3-phosphate dehydrogenase |
| GC | Group-specific component (vitamin D binding protein) |
| GSTA2 | Glutathione S-transferase A2 |
| HAGH | Hydroxyacylglutathione hydrolase |

TABLE 1-continued

Upregulated Genes

| | |
|---|---|
| HAMP | Hepcidin antimicrobial peptide |
| HP | Haptoglobin |
| HPN | Hepsin (transmembrane protease, serine 1) |
| HPX | Hemopexin |
| HSD11B1 | Hydroxysteroid (11-beta) dehydrogenase 1 |
| ICAM1 | Intercellular adhesion molecule-1 |
| ID1 | Inhibitor of differentiation-1 |
| IL10 | Interleukin-10 |
| IL18 | Interleukin-18 |
| ITIH1 | Inter-alpha (globulin) inhibitor H1 |
| ITIH4 | Inter-alpha (globulin) inhibitor H4 (plasma Kallikrein-sensitive glycoprotein) |
| KCNK7 | Potassium channel, subfamily K, member 7 |
| KNG1 | Kininogen 1 |
| LECT2 | Leukocyte cell-derived chemotaxin 2 |
| LPA | Lipoprotein, Lp(a) |
| LRP1 | Low density lipoprotein receptor- ela ed protein 1 |
| MAT1A | Methionine adenosyltransferase I, alpha |
| MRC1 | Mannose receptor, C type 1 |
| MST1 | Macrophage stimulating 1 (hepatocyte growth factor-like) |
| MT1A | Metallothionein 1A |
| MT1B | Metallothionein 1B |
| MT1E | Metallothionein 1E |
| NR1I3 | Nuclear receptor subfamily 1, group 1, member 3 |
| ORM1 | Orosomucoid 1 |
| ORM2 | Orosomucoid 2 |
| PCK2 | Phosphoenolpyruvate carboxykinase 2 (mitochondrial) |
| PLG | Plasminogen |
| PON3 | Paraoxonase 3 |
| POR | P450 (cytochrome) oxidoreductase |
| PRDX4 | Peroxiredoxin 4 |
| PXM P2 | Peroxisomal membrane protein 2, 22kDa |
| PYROXD1 | Pyridine nucleotide-disulphide oxidoreductase domain 1 |
| RBP4 | Retinol binding protein 4, plasma |
| SAA4 | Serum amyloid A4, constitutive |
| SEPP1 | Selenoprotein P, plasma, 1 |
| SERPINA1 | Serpin peptidase inhibitor, clade A, member 1 |
| SERPINA6 | Serpin peptidase inhibitor, clade A, member 6 |
| SERPINC1 | Serpin peptidase inhibitor, clade C (antithrombin), member 1 |
| SERPIND1 | Serpin peptidase inhibitor, clade D (heparin cofactor), member 1 |
| SLC13A2 | Solute carrier family 13, member 2 |
| 5L027A5 | Solute carrier family 27 (fatty acid transporter), member 5 |
| SPP2 | Secreted phosphoprotein 2, 24kDa |
| TF | Transferrin |
| TGFB1 | Transforming growth factor, beta 1 |
| THNSL2 | Threonine synthase-like 2 (S. cerevisiae) |
| TM4SF4 | Transmembrane 4 L six family member 4 |
| TNFA | Tumor necrosis factor-alpha |
| TNFSF14 | Tumor necrosis factor (ligand) superfamily, member 14 |
| TSPAN9 | Tetraspanin 9 |
| TTR | Transthyretin (prealbumin, amyloidosis type I) |
| TXN | Thioredoxin |
| UGT1A6 | UDP glucuronosyltransferase 1 family, polypeptide A4 |
| UGT2B7 | UDP glucuronosyltransferase 2 family, polypeptide B7 |
| VEGFA | Vascular endothelial growth factor A |
| VTN | Vitronectin |
| ZGPAT | Zinc finger, CCCH-type with G patch domain |

Table 2 below lists 28 genes whose expression levels were more than two-fold-downregulated in tumor-unaffected hepatic tissue compared to the expression in metastatic tissue and peripheral blood mononuclear cells from Stage IV patients with CRC having systemic metastasis disease. In bold are ten genes whose expression levels were downregulated in liver parenchymal and non-parenchymal sinusoidal cells given the conditioned medium from cultured CRC cells (HT-29 CRC cell line). This gene subset was also selected for further analysis.

TABLE 2

Downregulated Genes

| | |
|---|---|
| ACTG1 | Actin, gamma 1 |
| ARPC2 | Actin related protein 2/3 complex, subunit 2, 34 kDa |
| BMP7 | Bone morphogenetic protein-7 |
| CALM1 | Calmodulin 1 (phosphorylase kinase, delta) |
| CAPG | Capping protein (actin filament), gelsolin-like |
| CEACAM1 | Carcinoembryonic antigen-related cell adhesion molecule 1 (biliary glycoprotein) |
| COL18A1 | Collagen, type xviii, alpha 1 |
| ERBB2IP | Erbb2 interacting protein |
| H2AFY | H2A histone family, member Y |
| H3F3B | H3 histone, family 3B (H3.3B) |
| HIST3H3 | Histone cluster 3, H3 |
| IFITM2 | Interferon induced transmembrane protein 2 (1-8D) |
| IGF1 | Insulin-like growth factor-1 |
| ING1 | Inhibitor of growth family, member 1 |
| NCL | Nucleolin |
| NGF | Nerve growth factor-beta |
| NOS2 | Nitric oxide synthase 2, inducible |
| PLP2 | Proteolipid protein 2 (colonic epithelium-enriched) |
| PPIA | Peptidylprolyl isomerase A (cyclophilin A) |
| RPIA | Ribose 5-phosphate isomerase A (ribose 5-phosphate epimerase) |
| RPL10 | Ribosomal protein L10 |
| RPS23 | Ribosomal protein S23 |
| RPS27 | Ribosomal protein S27 (metallopanstimulin 1) |
| RPS3A | Ribosomal protein S3A |
| SDC1 | Syndecam-1 |
| TMSB10 | Thymosin, beta 10 |
| TUBA4A | Tubulin, alpha 4a |
| YWHAB | Tyrosine 3-monooxygenase/tryptophan 5-monooxygenase activation protein, beta polypeptide |

Table 3 below shows liver prometastatic gene families (Inflammatory, Immune Regulation, Metabolic Bioprotection, and Fibrogenic Regeneration) of the thirty-one, two-fold upregulated and two-fold down-regulated genes of Tables 1 and 2 whose altered expression level in tumor-unaffected hepatic tissue is associated with liver metastasis growth in patients with CRC. The functional gene classification activity was performed manually by accessing the Gene Ontology and PubMed databases and is based on known biopathological functions assigned individually to studied genes. Below in Table 3 are listed and sorted by functional categories these 31 liver prometastatic genes.

TABLE 3

Liver Prometastatic Genes Sorted by Functional Categories

| Metabolic Bioprotection Genes | Immune Regulation Genes | Inflammatory Genes | Fibrogenic Regenerative Genes |
|---|---|---|---|
| TXN | KNG1 | ID-1 | RPS27 |
| PRDX4 | CEACAM-1 | IL-18 | RPS23 |
| NOS2 | BMP-7 | TNF-alpha | DDR2 |
| GAPDH | SDC-1 | VEGF-A | TGFB1 |
| MTE1 | COL18-A1 | EPHA-1 | VTN |
| HP | IL-10 | TNFSF14 | NGF |
| CRP | ICAM-1 | CYP2E1 | IGF-1 |
| ERBB21P | MRC1 | ADH18 | |

A first teaching of the present invention concerns identifying metastasis- associated genes in the tumor-unaffected hepatic tissue of Stage-IV cancer patients with metastatic CRC. As discussed in connection with FIG. 1, comparative transcriptome profiling using RNA from hepatic CRC metastases, tumor-unaffected hepatic tissue, and peripheral mononuclear blood cells uncovers approximately 122 genes specifically over-expressed and approximately 28 genes specifically under-expressed, each group being more than two-fold overexpressed or under-expressed in tumor-unaffected hepatic tissue from Stage-IV cancer patients with metastatic CRC. These genes are identified in Tables 1-2 above. Upregulated and downregulated gene sets were selected for further analysis. Transcriptome profiling was obtained from surgically removed liver specimens and archived biopsies of patient tissue. Table 3 shows a subset of these liver-associated genes (over-expressed and under-expressed genes) isolated according to their association with cancer-related cellular functions of inflammation, immune regulation, metabolic bioprotection and regeneration, i.e., functional categories. Further laboratory tests were performed on this subset of liver-associated genes to categorize them according to additional prometastatic criteria including (1) altered expression level in tumor-unaffected hepatic tissue associated with liver metastasis growth in patients with CRC, (2) altered expression in cultured liver parenchymal and non-parenchymal cells exposed to soluble factors from cultured CRC cells, and (3) altered expression associated with experimental hepatic colonization and growth of circulating CRC cells in animal models of CRC.

Table 4 below shows actual clinical data taken from forty-five patients (29 patients with CRC and 16 without CRC) that were included in the study on the expression pattern of liver prometastatic genes in hepatic biopsies from patients with and without CRC where TNM indicates tumor node metastasis stage.

TABLE 4

| Clinical Parameters | Patients with CRC | | Patients without CRC | |
| --- | --- | --- | --- | --- |
| | No. | % | No. | % |
| Gender | | | | |
| Female | 10 | 34 | 8 | 50 |
| Male | 19 | 66 | 8 | 50 |
| Average Age | 58 | — | 57 | — |
| Metabolic Syndrome | 14 | 48 | 7 | 43 |
| Cholelithiasis | 0 | 0 | 16 | 100 |
| TNM stage | | | | |
| I | 0 | 0 | 0 | 0 |
| II | 0 | 0 | 0 | 0 |
| III | 12 | 42 | 0 | 0 |
| IV | 17 | 58 | 0 | 0 |
| Tumor localization | | | | |
| Left-sided Colon | 11 | 39 | 0 | 0 |
| Right-sided Colon | 10 | 34 | 0 | 0 |
| Rectum | 6 | 20 | 0 | 0 |
| Others (gastric, duodenum) | 2 | 7 | 0 | 0 |

Table 5 below shows measurement data indicative of the thirty-one two-fold plus upregulated and down-regulated liver prometastatic gene expression levels under investigation in patients with and without CRC, The data shown therein represents average normalized (Ct Ratio of studied geneiCt of constitutive gene) Ct (cycle threshold) values ±SD (standard deviation) as well as mean probability values "p-values,"

TABLE 5

| | | Average Ct. Norm. | T-Student (p Value) | U-Mann Whitney (p Value) |
| --- | --- | --- | --- | --- |
| GAPDH | With CRC | 0.822 | 0.118 | 0.136 |
| | Without CRC | 0.812 | | |
| TXN | With CRC | 0.856 | 0.549 | 0.436 |
| | Without CRC | 0.852 | | |
| PRDX4 | With CRC | 0.878 | | 0.086 |
| | Without CRC | 0.892 | | |
| MT1E | With CRC | 0.970 | 0.026 | 0.014 |
| | Without CRC | 1.000 | | |
| ERBB2IP | With CRC | 0.965 | 0.010 | 0.010 |
| | Without CRC | 0.949 | | |
| NOS2 | With CRC | 1.175 | | 0.084 |
| | Without CRC | 1.193 | | |
| HP | With CRC | 0.624 | 0.775 | 0.335 |
| | Without CRC | 0.627 | | |
| CRP | With CRC | 0.833 | 0.004 | 0.002 |
| | Without CRC | 0.908 | | |
| BMP7 | With CRC | 1.327 | 0.514 | 0.348 |
| | Without CRC | 1.309 | | |
| SDC1 | With CRC | 0.921 | | 0.045 |
| | Without CRC | 0.893 | | |
| IGF1 | With CRC | 0.975 | 0.593 | 0.741 |
| | Without CRC | 0.970 | | |
| COL18A1 | With CRC | 0.842 | | 0.013 |
| | Without CRC | 0.821 | | |
| ICAM1 | With CRC | 0.965 | | 0.000 |
| | Without CRC | 1.019 | | |
| KNG1 | With CRC | 0.794 | | 0.042 |
| | Without CRC | 0.776 | | |
| IL10 | With CRC | 1.081 | 0.000 | 0.000 |
| | Without CRC | 1.130 | | |
| CEACAM1 | With CRC | 0.963 | 0.878 | 0.864 |
| | Without CRC | 0.962 | | |
| MRC1 | With CRC | 0.976 | | 0.000 |
| | Without CRC | 1.018 | | |
| EPHA1 | With CRC | 1.032 | 0.002 | 0.002 |
| | Without CRC | 1.002 | | |
| TNFSF14 | With CRC | 0.988 | | 0.025 |
| | Without CRC | 1.018 | | |
| CYP2E1 | With CRC | 0.717 | 0.000 | 0.000 |
| | Without CRC | 0.688 | | |
| ADH1B | With CRC | 0.734 | 0.001 | 0.001 |
| | Without CRC | 0.698 | | |
| ID1 | With CRC | 0.908 | 0.007 | 0.001 |
| | Without CRC | 0.935 | | |
| TNF | With CRC | 1.060 | 0.000 | 0.000 |
| | Without CRC | 1.164 | | |
| IL18 | With CRC | 1.052 | 0.000 | 0.000 |
| | Without CRC | 1.114 | | |
| VEGFA | With CRC | 0.910 | 0.882 | 0.792 |
| | Without CRC | 0.911 | | |
| RPL23 | With CRC | 0.807 | 0.766 | 0.712 |
| | Without CRC | 0.808 | | |
| RPS27 | With CRC | 0.763 | 0.148 | 0.178 |
| | Without CRC | 0.755 | | |
| VTN | With CRC | 0.707 | | 0.428 |
| | Without CRC | 0.702 | | |
| NGF | With CRC | 1.141 | 0.019 | 0.007 |
| | Without CRC | 1.113 | | |
| TGFB1 | With CRC | 0.972 | 0.934 | 0.989 |
| | Without CRC | 0.973 | | |
| DDR2 | With CRC | 1.045 | 0.438 | 0.421 |
| | Without CRC | 1.038 | | |

Figure 2:
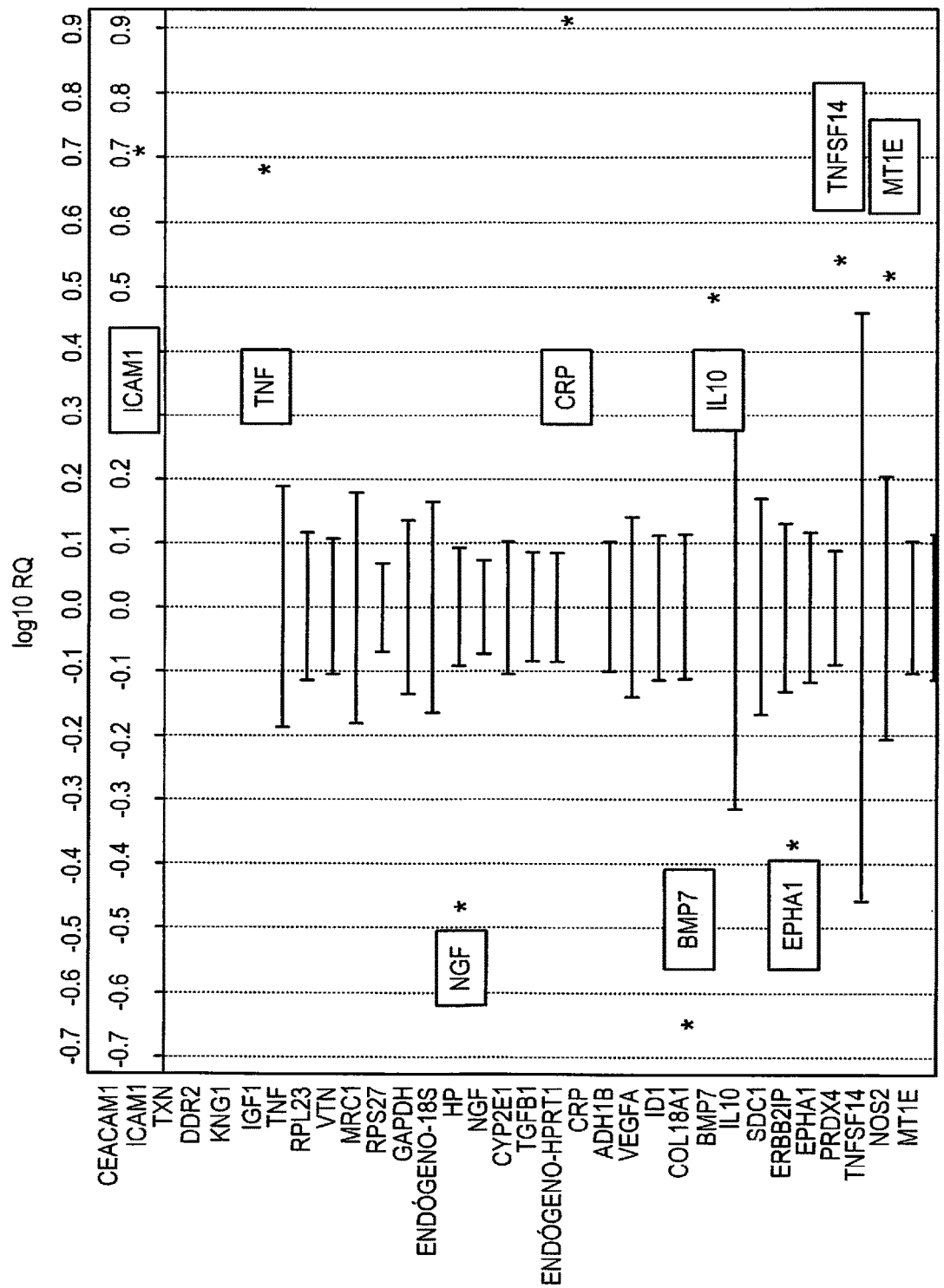
FIG. 2 shows a logarithmic scale representation of the relative quantification (RQ) values of the liver prometastatic gene expression in CRC patients with respect to same values in patients without CRC.

FIG. 2 depicts a logarithmic scale representation of the relative quantification (RQ) values of liver prometastatic gene expressions in CRC patients with respect to same values in patients without CRC. Error bars indicate maximum and minimum RQ values. "*" indicates statistically significant values where $p<0.05$.

Figure 3:
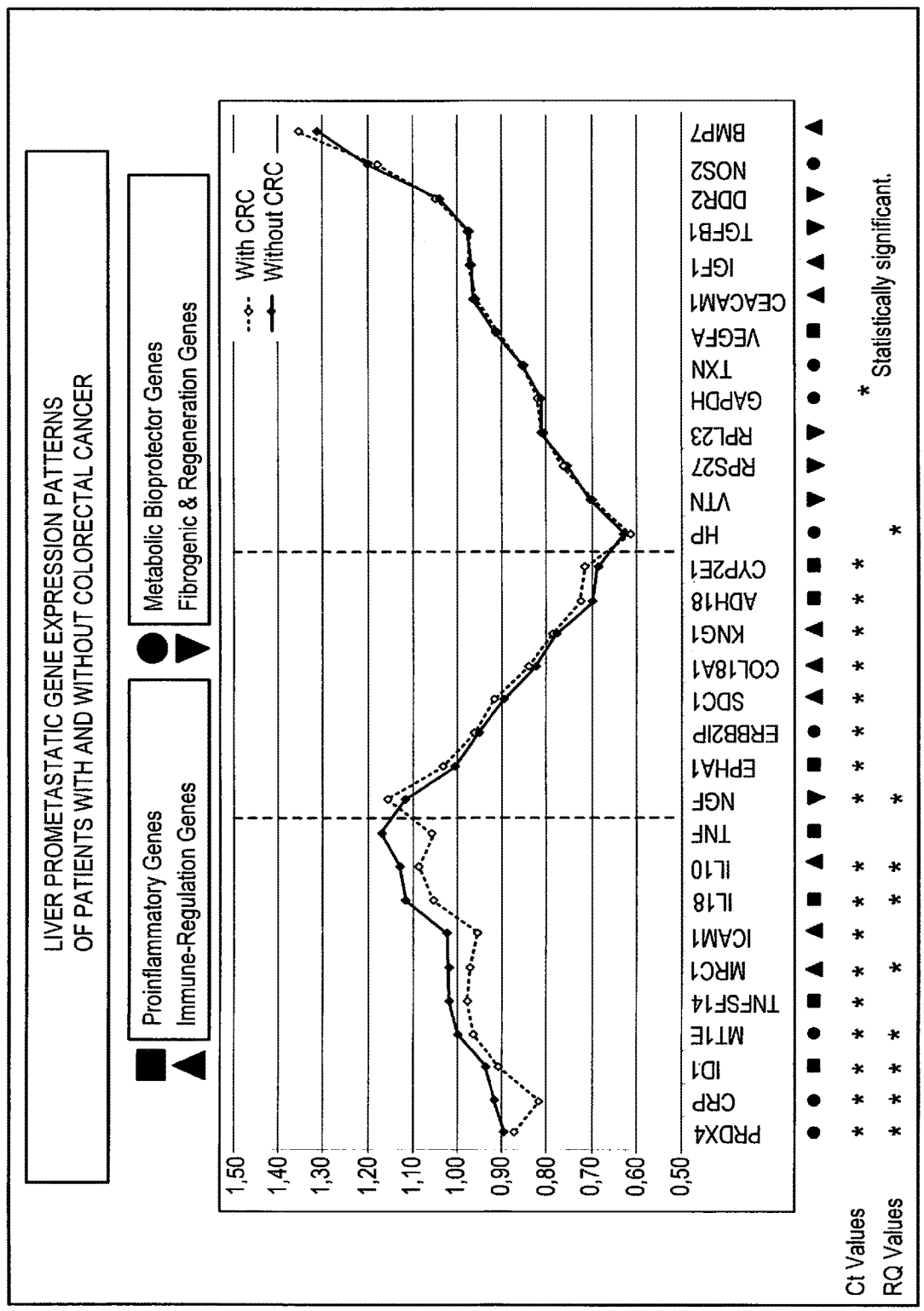
FIG. 3 shows divergent liver prometastatic gene expression patterns in patients with and without CRC.

FIG. 3 depicts liver prometastatic gene expression patterns (color-coded in provisional application according to functional category but here, ■ indicates proinflammatory genes, ▲ indicates immune-regulation genes, ● indicates metabolic bioprotection genes, and ▼ indicates fibrogenic and regeneration genes) in patients with and without CRC. Differences between patients with and without CRC were statistically significant according to a U-Man Whitney test (p<0.05). Statistically significant genes are identified by "*" denoted in the lower legend of FIG. 3. Advantageously, by examining the expression levels of one or more statistically significant genes in group 1 and/or group 2 of patients with CRC relative to a control (i.e., gene expression levels of persons free of CRC), rather than waiting for clinical signs to become apparent by imaging or non-biochemical changes in the microenvironment, one may detect metastatic cancer in the hepatic biochemical microenvironment to enable very early treatment and potential eradication of metastatic cancer cells.

An aspect of the invention includes a complementary diagnostic test to detect "liver prometastatic reaction level and class" in patients with CRC without metastatic disease. Expression of liver prometastatic genes in hepatic tissue selected above was next studied in twenty-nine patients with CRC (at stages III and IV) and sixteen patients without CRC used as controls. Table 4 details clinical information about the patients involved in the study. Based on normalized Ct values, Table 5 shows average values of the gene expression levels for the 31 genes involved for the 29 patients with CRC. As reflected in FIG. 3, expression levels were significantly (probability p<0.05) increased for ten liver prometastatic genes (group 1) and decreased in eight genes (group 2), with non-statistically significant (i.e., insignificant) changes in twelve to thirteen genes, when comparing patients with (29 patients) and without (16 patients) CRC. The vertical axis of FIG. 3 reflects the relative $C_t$ data relative to a control, or ratio of the $C_t$ cycle count (i.e., Ct value) of the sample under examination relative to the $C_t$ cycle count of a control $C_t$ value, Regarding group 1 genes of patients with CRC, i.e., the dotted trace, detection of an expression level signal at a lower cycle count $C_t$ in the PCR process indicates a higher gene expression level. Detection of an expression level signal for each of the group 2 genes of patients with CRC occurred at a higher cycle count $C_t$ as reflected in the middle portion of the dotted trace of FIG. 3. However, no statistically significant changes in gene expression levels of this latter group of twelve to thirteen genes (group 3) were detected when comparing CRC patients with and without hepatic metastases (or between CRC patients and CRC-free patients as controls) suggesting that detected liver prometastatic gene expression changes in tumor unaffected hepatic tissue nevertheless occurred in the liver of CRC patients irrespective of having or not having metastases. In addition, correlation of respective gene expression levels of group 3 genes was deemed required to validate the efficacy of the relative expression levels of group 1 and group 2 genes. In other words, without congruence of the expression levels of patients with and without CRC among group 3 genes, the conditions denoted for group 1 and group 2 genes would not be valid.

FIG. 4A-4D and Table 6 further indicate that expression levels of the various genes differ according to the anatomical location of the patient's primary CRC, i.e., in the rectum, left-side colon or the right-side colon. Therefore, a liver prometastatic reaction occurs in the liver of patients with CRC prior to metastasis development and, in accordance with another aspect of the invention, by scoring number and intensity of gene changes we may determine the Liver Prometastatic Reaction Level, which may be helpful to determine or assess prometastatic hepatic cancer risk.

In addition, the majority of proinflammatory (seven out of eight) and immune regulation (six out of nine) liver prometastatic genes, but only a minority of fibro-regenerative (one out of five) and metabolic bio-protective (three out genes eight) were significantly (p<0.05) changed in patients with CRC versus patients without CRC (Table 3, FIGS. 1 and 2). This suggests that in addition to the number of changed genes, the kind of changed genes in functional terms defines the Liver Prometastatic Reaction Class in the liver of patients with CRC. Both number and functional categories of liver prometastatic genes changed in patients with CRC may serve as a Complementary diagnostic test for the quantitative assessment of liver metastasis risk and recurrence in patients with CRC, and thus, may form the basis of a rule-based method of detecting occult CRC subclinically in patients having no clinical symptoms of CRC. A rule-based processing system to receive data inputs and appropriate program instructions may be utilized to automatically output this determination on a display device or other output,

TABLE 6

Liver prometastatic gene expression level by functional category and anatomic location of the primary CRC

| Liver Prometastatic Genes | Gene Expression Level | RECTUM | LEFT-SIDED COLON | RIGHT-SIDED COLON |
|---|---|---|---|---|
| PROINFLAMMATORY GENES | HIGH | — | IL18 ID1 TNF TNFSP14 ADH1B | ID1 TNF |
|  | LOW | IL18 ID1 VEGFA TNFSF14 ADH1B CYP2E1 | — | ADH1B CYP2E1 |
| IMMUNO REGULATION GENES | HIGH | IL10 MRC1 | ICAM1 MRC1 KNG1 SDC1 | IL10 MRC1 BMP7 |
|  | LOW | ICAM1 KNG1 SOC1 IGF1 BMP7 | BMP7 | KNG1 SOC1 |
| METABOLIC BIOPROTECTION GENES | HIGH | NOS2 | PRXD4 MTE1 HP NOS2 CRP | — |
|  | LOW | GAPDH TXN MTE1 HP CRP ERBB2IP | TXN | — |
| FEROGENIC AND REGENERATION GENES | HIGH | — | VTN | — |
|  | LOW | VTN | RLP23 TGFB1 NGF | VTN NGF |

FIG. 5 shows proinflammatory gene expressions in liver from patients with and without CRC. Data are represented as increasing distribution of mean values. Data express normalized Ct values (Ct Ratio of studied gene/Ct of constitutive gene). The discontinuous line marks the intermediate point between the minimum and maximum ratios obtained for each gene (Y axis) for total number of analyzed samples (X axis) from patients with and without CCR, FIG. 6 depicts immuno-regulation gene expressions in liver from patients with and without CRC, Data are represented as increasing distribution of mean values, Data express normalized Ct values (Ct Ratio of studied gene/Ct of constitutive gene). The discontinuous line marks the intermediate point between the minimum and maximum ratios obtained for each gene (Y axis) for total number of analyzed samples (X axis) from patients with and without CCR.

FIG. 7 depicts metabolic bioprotection gene expressions in liver from patients with and without CRC. Data are represented as increasing distribution of mean values. Data express normalized Ct values (Ct Ratio of studied gene/Ct of constitutive gene). The discontinuous line marks the intermediate point between the minimum and maximum ratios obtained for each gene (Y axis) for total number of analyzed samples (X axis) from patients with and without CRC.

FIG. 8 depicts fibrogenic and regeneration gene expressions in liver from patients with and without CRC. Data are represented as increasing distribution of mean values. Data express normalized Ct values (Ct Ratio of studied gene/Ct of constitutive gene). The discontinuous line marks the intermediate point between the minimum and maximum ratios obtained for each gene (Y axis) for total number of analyzed samples (X axis) from patients with and without CRC.

Based on analyses illustrated in FIGS. 5-8, another aspect of the invention includes a complementary diagnostic test to provide an alert of possible occult CRC in patients without clinical evidence of CRC but with other digestive system diseases that increase CRC risk, such as cholelithiasis and metabolic syndrome. Comparative distribution of gene expression levels of selected genes of studied CRC patients and their controls without CRC, by their expression of liver prometastatic genes (as indicated by the analyses shown in FIGS. 5-8) demonstrate that those genes best contributing to the segregation of patients with and without CRC are Metabolic bioprotection genes PRDX4, MT1E, CRP and NOS2; Immune regulation genes ICAM1, IL10 and MRC1; and Proinflammatory genes ID1, TNF-a, IL18 and TNFSF14. All of these genes remarkably increased their expression levels in patients with CRC while decreased their expression levels in patients without CRC. On the contrary, immune-regulation genes SDC1, COL18A1 and KNG1, Proinflammatory genes EPHA1, CYP2E1, ADH1B, and fibrogenic/regeneration gene NGF increased their expression levels in patients without CRC while decreased their expression levels in patients with CRC, as indicated in FIGS. 5-8.

Figure 9:
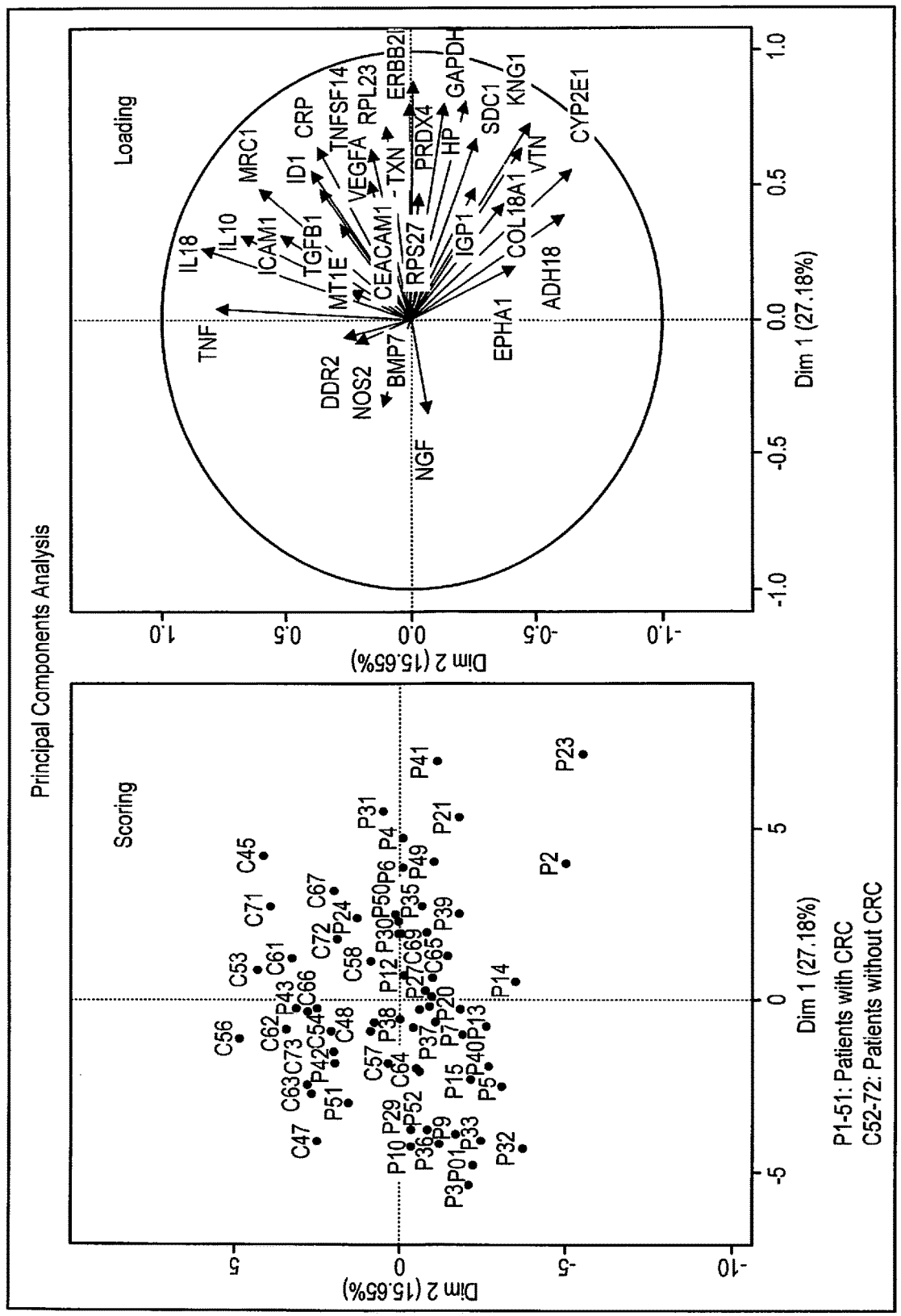
FIG. 9 show comparison of overall expression profiles across samples from patients with and without CRC via a principal component analyses (PCA) of gene expressions in patients (P1-P51) with and in patients (C52-C72) without CRC where a first principal component (Dim 1) reveals a 27.18% of the variation and a second (Dim 2) reveals a 15.65% variation that separated most of patients with CRC from patients without CRC.

FIG. 9 shows a comparison of overall expression profiles across samples from patients with and without CRC in respective Scoring value and Loading value charts. Scoring chart of FIG. 9 shows results for a Principal Component Analyses (PCA) of the data, which is used to emphasize variations and reveal data patterns of gene expressions in patients with (P1-P51) and without (C52-C72) CRC. The first principal component (Dimension 1) sets forth a 27.18% variation, whereas the second Dimension 2 sets forth a 15.65% variation. It is seen that Dimension 2 separated most of patients with CRC from patients without CRC.

A principal component analysis (PCA), multivariate regression analysis used to distinguish samples with multiple measurements was conducted, the results of which are shown in FIG. 9B. Supervised discriminant analysis showed that liver prometastatic immune regulation and proinflammatory genes were the most discriminative for patients with and without CRC.

Figure 10A:
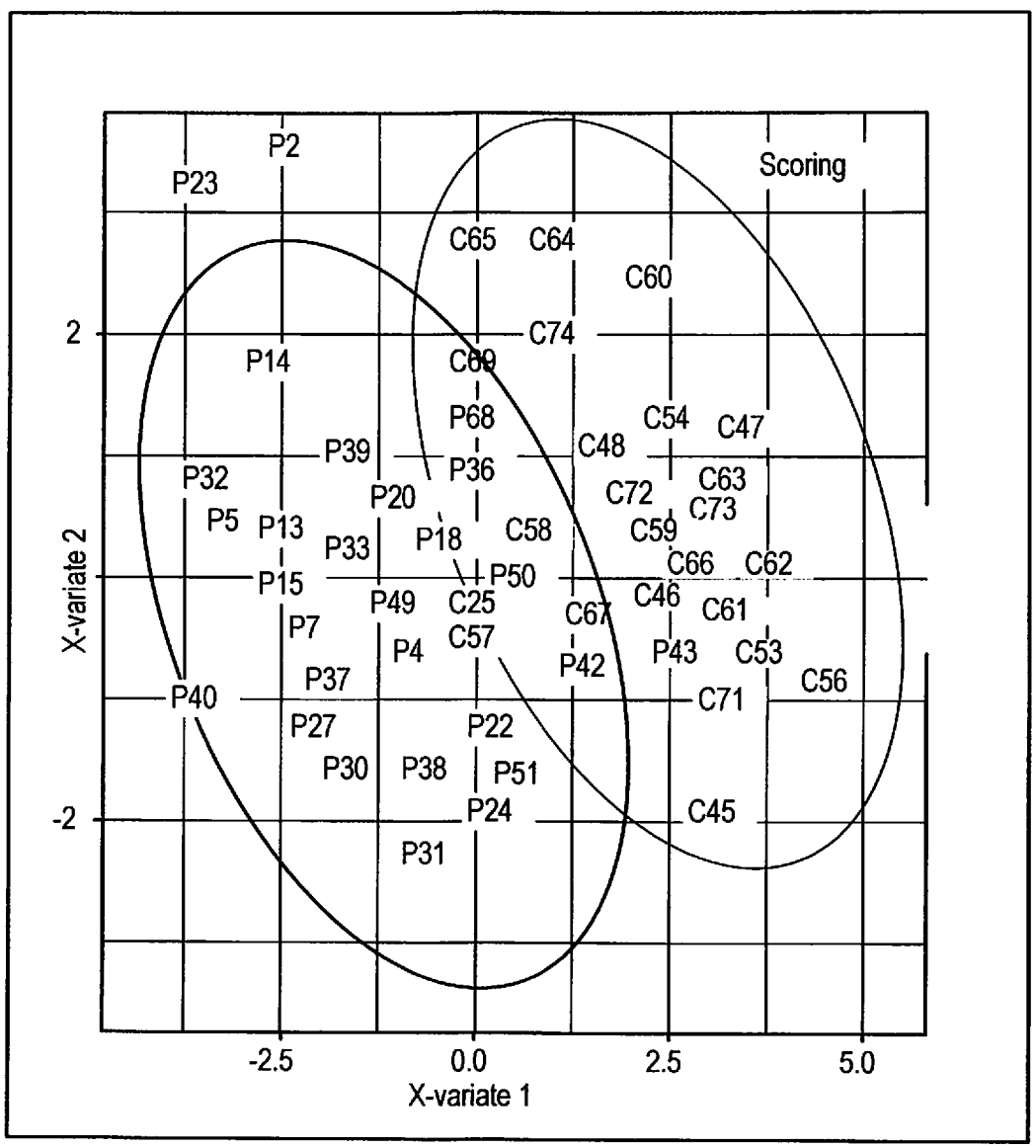
FIGS. 10A and 10B show Partial Least Squares-Discriminant Analysis (PLS-DA) intended to discriminate patients with and without CRC based on their hepatic expression level of liver prometastatic genes where elliptical shapes of FIG. 10A adopted by lines define the position coordinates of included patients (C indicates patients without CRC and P indicates patients with CRC). In this case, the discriminatory capacity was associated with the first component in the analysis.
Figure 10B:
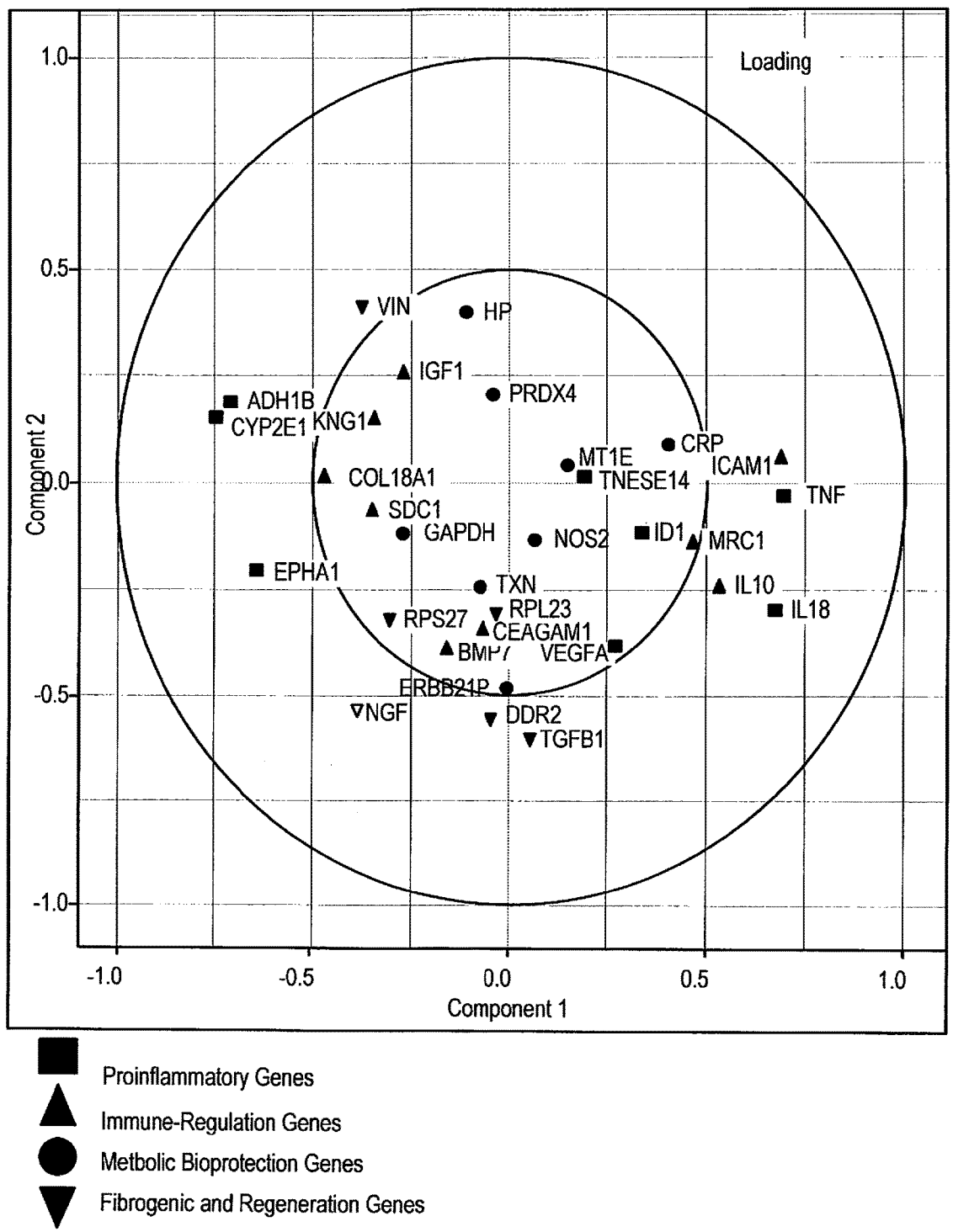

FIGS. 10A and 10B show a Partial Least Squares-Discriminant Analysis (PLS-DA) of gene expression data in respective Scoring and Loading plots, which is intended to discriminate between patients with and without CRC based on their hepatic expression levels of liver prometastatic genes. FIG. 10A depicts elliptical shapes adopted by lines that define the position coordinates of included patients (patients C52-72 without CRC and patients P1-51 with CRC). In this case, the discriminant capacity was associated with the first component in the analysis. FIG. 10B depicts position coordinates of liver prometastatic genes plotted in correlation circles whose diameters define influence of the genes in the prediction of the class of patient. In this case, metabolic bioprotection and fibrogenic/regeneration genes are in the smaller circle, indicating that their expression levels had less ability to predict the patient's class than Immune regulation and proinflammatory genes mainly located in the large correlation circle, which indicates a greater predictive capacity of the patient class.

FIGS. 10A and 10B show results of a supervised discriminant analysis (i.e., a Partial Least Squares-Discriminant Analysis, PLS-DA) to classify genes and patients by their correlation and ability to predict patients with and without CRC. The elliptical shapes adopted by lines in FIG. 10A define position coordinates of included patients and show that the discriminant capacity was associated with the first component in the analysis. Next, position coordinates of studied liver prometastatic genes were plotted in correlation circles, whose diameters define the influence of the genes in the prediction of the class of patient (FIG. 10B). Studied genes were distributed in correlation circles according to their functional category and once again, metabolic bioprotection and fibrogenic/regeneration genes were in the smaller circle, indicating that their expression levels had less ability to predict the patient's class, while Immune regulation and proinflammatory genes were mainly located in the large correlation circle, indicating their greater predictive capacity of the patient class.

Figure 11A:
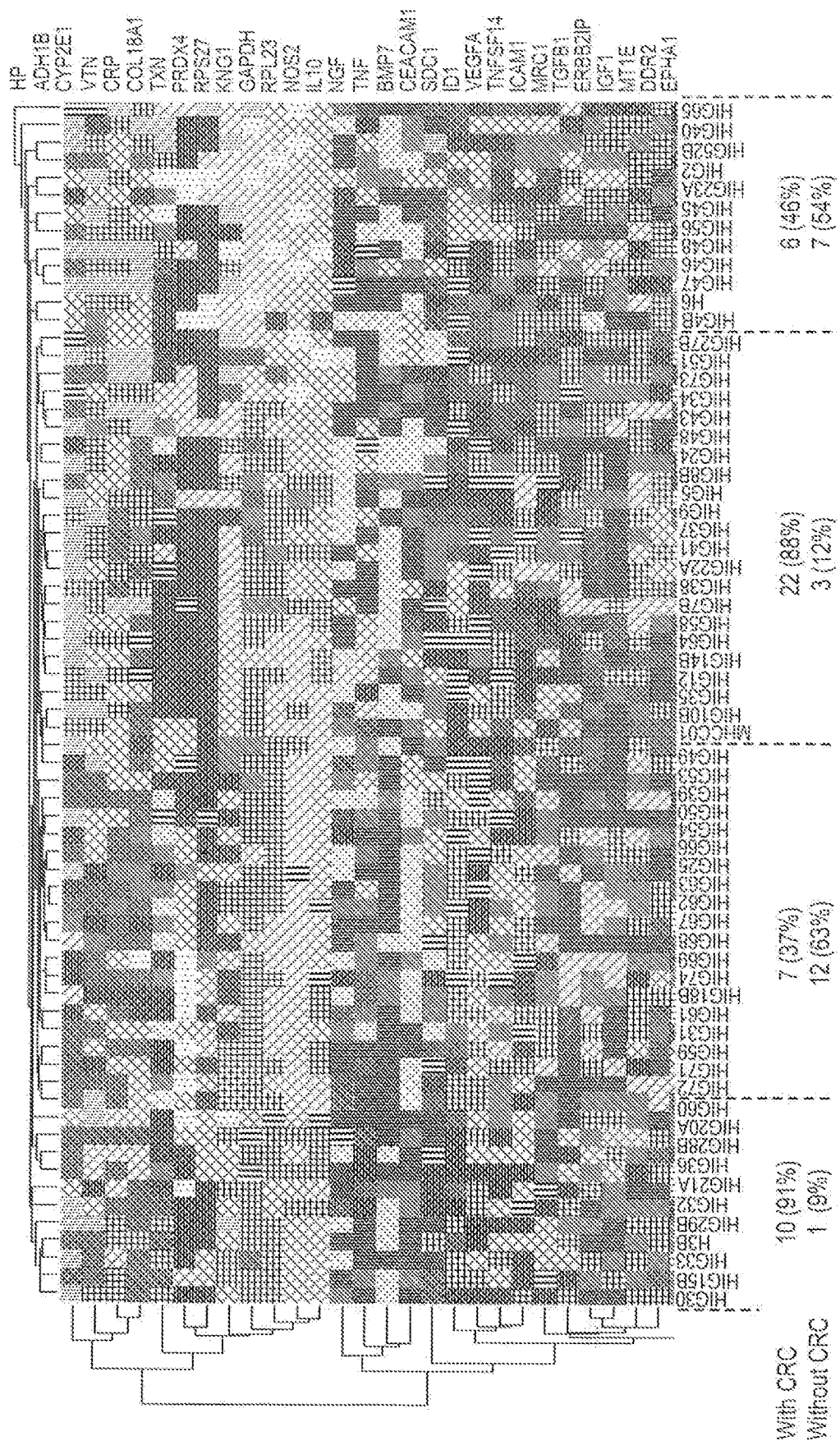
FIGS. 11A and 11B show heatmaps of clustering data for patients with and without CRC according their liver prometastatic gene expression patterns based on ΔΔLCt ratios.
Figure 11B:
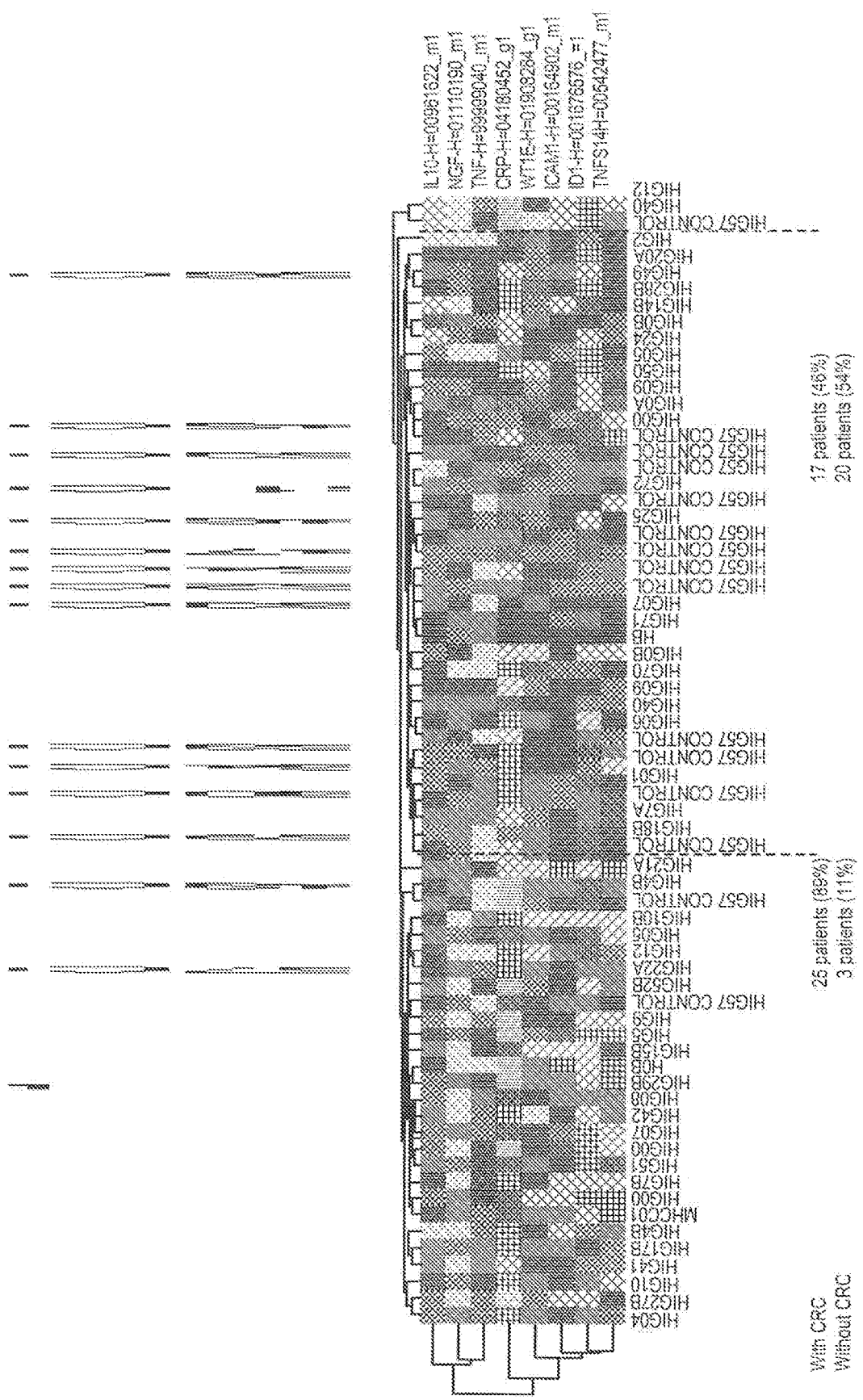

FIGS. 11A-11B show heatmaps for clustering patients with and without CRC according their liver prometastatic gene expression patterns based on ΔΔCt ratio. FIG. 11A shows four subgroups of patients with distinct gene expression patterns, two of them being enriched by patients with CRC and the two others by patients without CRC. FIG. 10B shows two subgroups with distinct gene expression patterns (genes with significant averages difference and significant RQ (relative quantization), enriched by either patients with or without CRC that were generated using the most discriminating genes. Some patients (noted in color green in the first and third groups) without CRC are seen to be grouped with patients with CRC suggesting they may have occult CRC (which was later confirmed by colonoscopy), while other patients with CRC (as noted in the second and fourth groups) were grouped with patients without CRC. Interesting, none of these ectopic CRC patients had hepatic metastases. Thus, according to yet another aspect of the present invention, manifestations of clustering provide a basis for early subclinical detection and pretreatment of occult CRC in patients lacking clinical symptoms.

An unsupervised hierarchical cluster analysis was performed to determine whether aggregation of genes by their expression similarity level per patient contributed to segregation of patients with and without CRC. Application of Euclidean distances between studied genes resulted in the appearance of clusters allowing the distribution of patients according to their transcriptional similarity levels. As shown in FIG. 11A, the heatmap outlined four mixed subgroups of patients with distinct gene expression patterns, two of them enriched by patients with CRC and the two others by patients without CRC. A new heatmap (FIG. 11B) was constructed using genes with the highest predictive power of the class of patient, as evidenced in the PLS-DA analysis. In this case, the power of discrimination was comparable to that obtained in the previous heatmap, but in this case there was a segregation in two large mixed subgroups rather than four, both of which being enriched either in patients with CRC or without CRC. Some patients without CRC are grouped with patients with CRC suggesting they may have occult CRC (which was later confirmed by colonoscopy), while some patients with CRC are grouped with patients without CRC (none of CRC patients had hepatic metastases), FIGS. 12A and 12B show Spearman's correlation of expression levels among liver prometastatic genes in patients with and without CRC. Only statistically significant ($p<0.05$ or higher) correlations with coefficient Rho equal to or greater than 0.7 were considered in this analysis. Nine of the ten correlations in patients with CRC involved five bioprotective genes (HP, ERBB2IP, GAPDH, CRP, PDRX4); four of these correlation gains were produced among bioprotective genes (ERBB2IP-GAPDH; ERBB2IP-PDRX4; CRP-GAPDH; CRP-HP), three among metabolic bioprotection and proinflammatory genes (CRP-TNFSF14; HP-TNFSF14; GAPDH-ID1) (CRP-NGF), immune-regulation genes (PDRX4-CEACAM1), as well as between proinflammatory and immune-regulation genes (TNFSF14-COL18A1). In contrast, eight out of the fourteen lost gene correlations in patients with CRC occurred in immune-regulation gene group (involving CEACAM1, MRC1, ICAM1, IL10, BMP7 genes), of which four were lost between immune-regulation and fibrogenic/regeneration genes (ICAM1-TGFB1; IL-10-NGF, CEACAM1-NGF, MRC1-NGF), whereas only two were lost between immune-regulation and proinflammatory genes (BMP7-TNF, CEACAM1-TNF) and another two among immune-regulation genes (CEACAM1-BMP7; MRC1-BMP7). There was also a striking loss of seven correlations between proinflammatory genes and other functional categories of genes (metabolic bioprotection, fibrogenic/regeneration and immune-regulation genes). Thus, in yet another aspect of the present invention, a statistically significant manifestation of a number and/or functional category of lost and new correlations of gene expression levels relative to such correlations in patients without CRD provides an additional rule-based system (the multigenic inter- and intra-functional group transcriptional relationships) and/or methodology to predict and treat occult CRC in patients lacking evidence of clinical symptoms.

FIGS. 13A-13D show hierarchical clustering performed based on Pearson's correlation Euclidean distance among the genes and gene dusters, and the results presented as a dendrogram plot in order to define the transcriptional structure of prometastatic genes in hepatic biopsies from patients without (Chart A) and with (Chart C) CRC. A cluster primarily including PRX4, SDC1, VEGFA, ID1 and CRP genes define the main change in the hepatic transcriptional structure between patients without and with CRC, as shown in Charts B and D. This analysis may be automated using data processing device or equipment. Thus, according to another aspect of the invention, hierarchical clustering of PRX4, SDC1, VEGFA, ID1 and CRP genes may form a subclinical parameter or indicator that is utilized by a data processing device to systematically automate prediction of CRC cancer risk and provide an alert of possible occult CRC in patients without clinical evidence of CRC but with other diseases that increase CRC risk.

Figure 12:
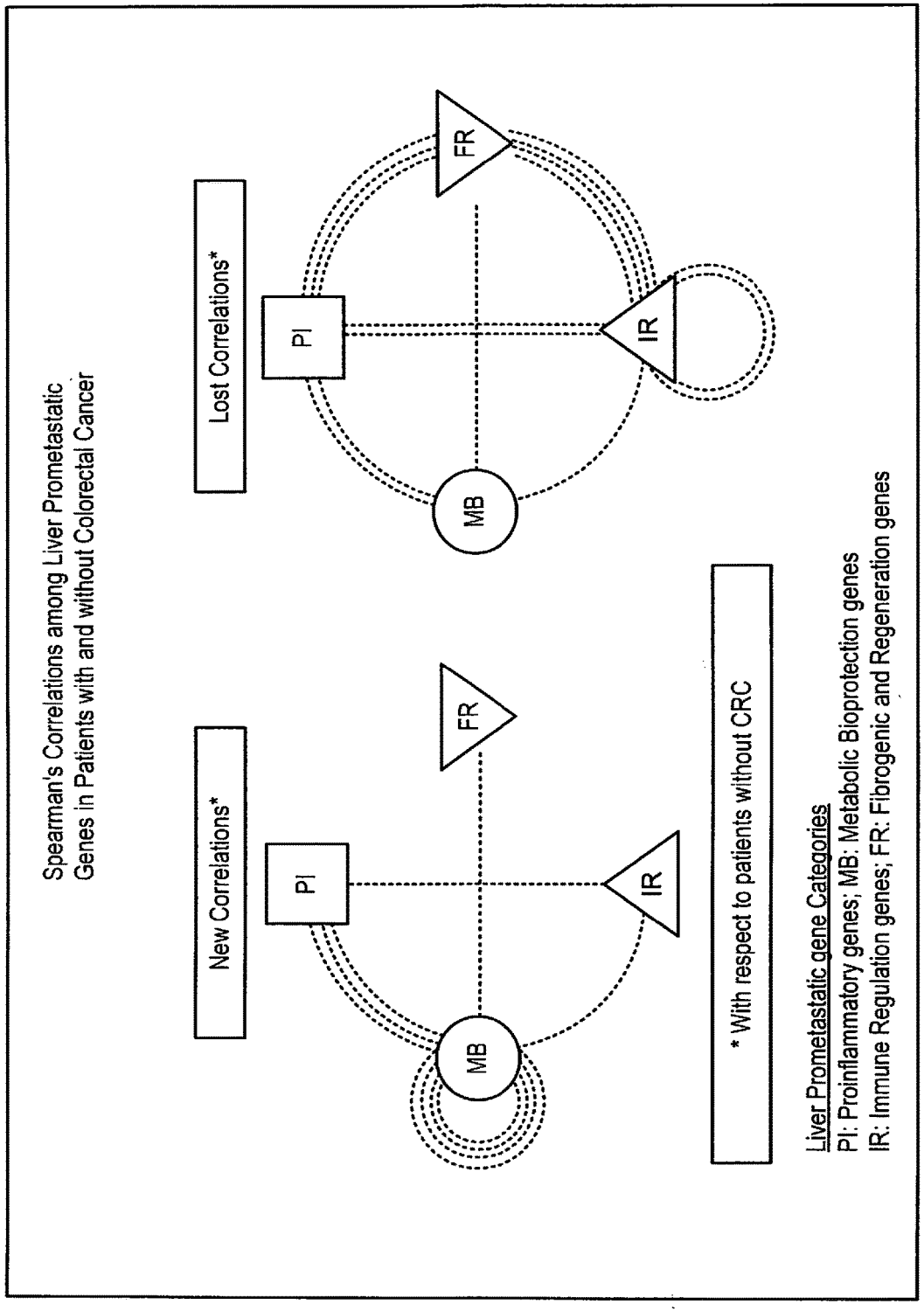
FIG. 12 shows Spearman's correlation patterns among liver prometastatic genes in patients with and without RCC.
Figure 13A:
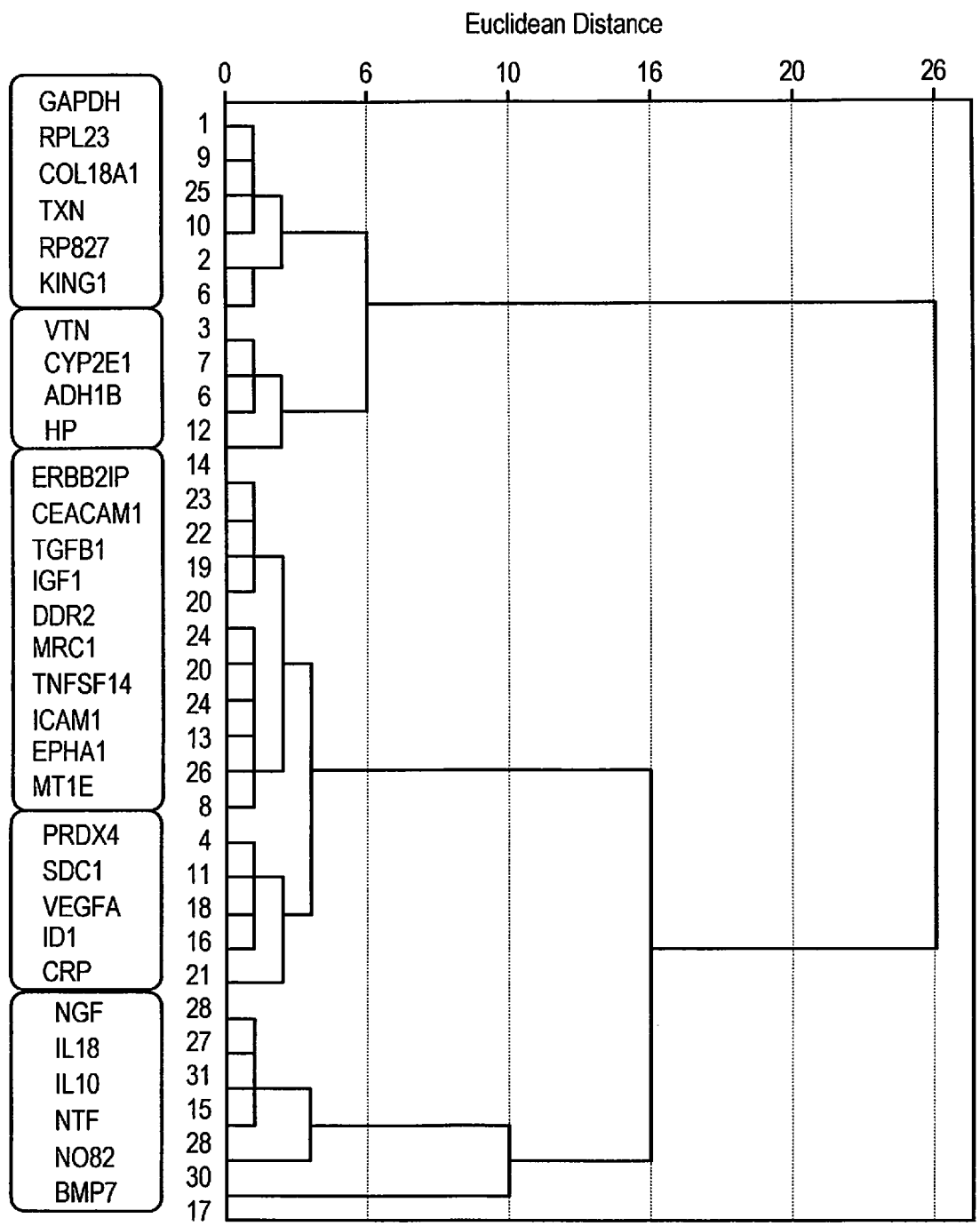
FIGS. 13A-13D show hierarchical clustering was performed based on Pearson's correlation of Euclidean distance among the genes and gene clusters, and the results presented as a dendrogram plot in order to define the transcriptional structure of prometastatic genes in hepatic biopsies from patients without and with CRC (FIGS. 13A and 13C) and where a cluster including PRX4, SDC1, VEGFA, ID1 and CRP genes defined a main change in the hepatic transcriptional structure between patients without and with CRC (FIGS. 13B and 13D).
Figure 13B:
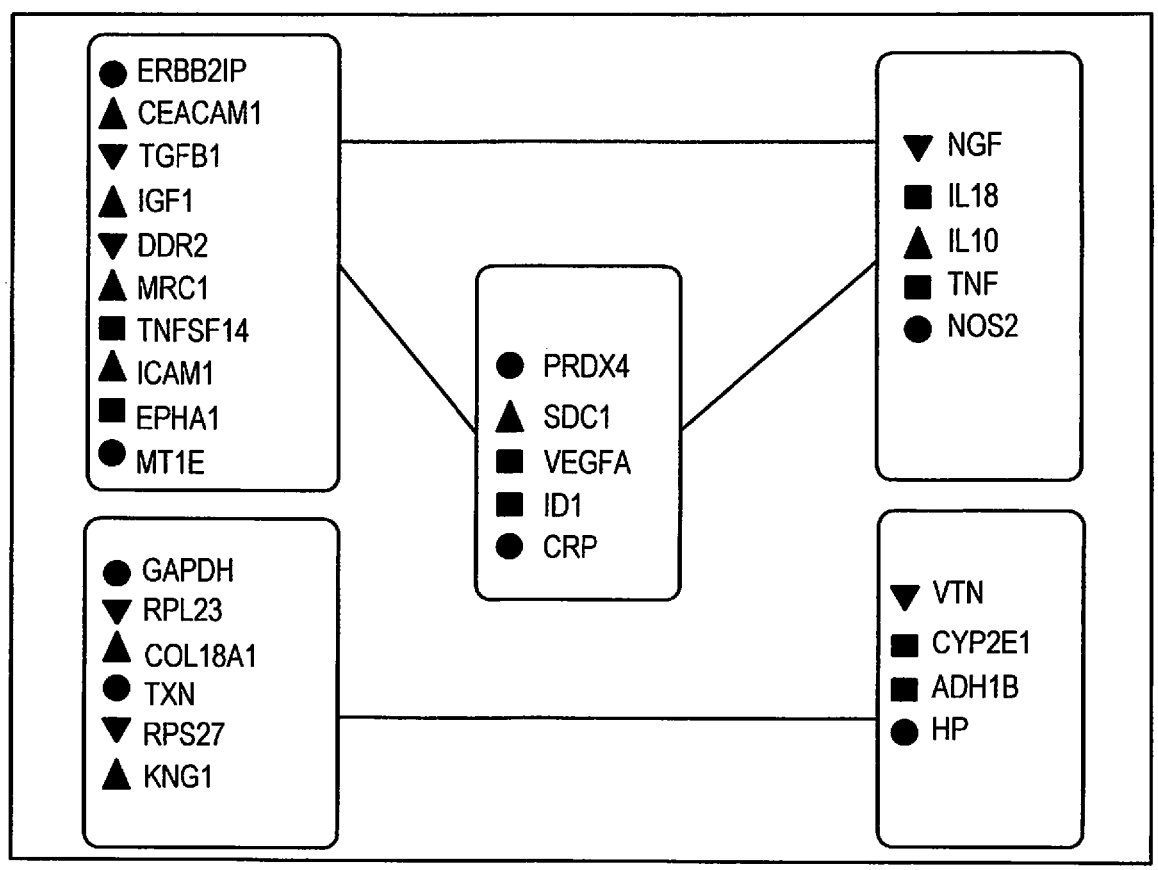
Figure 13C:
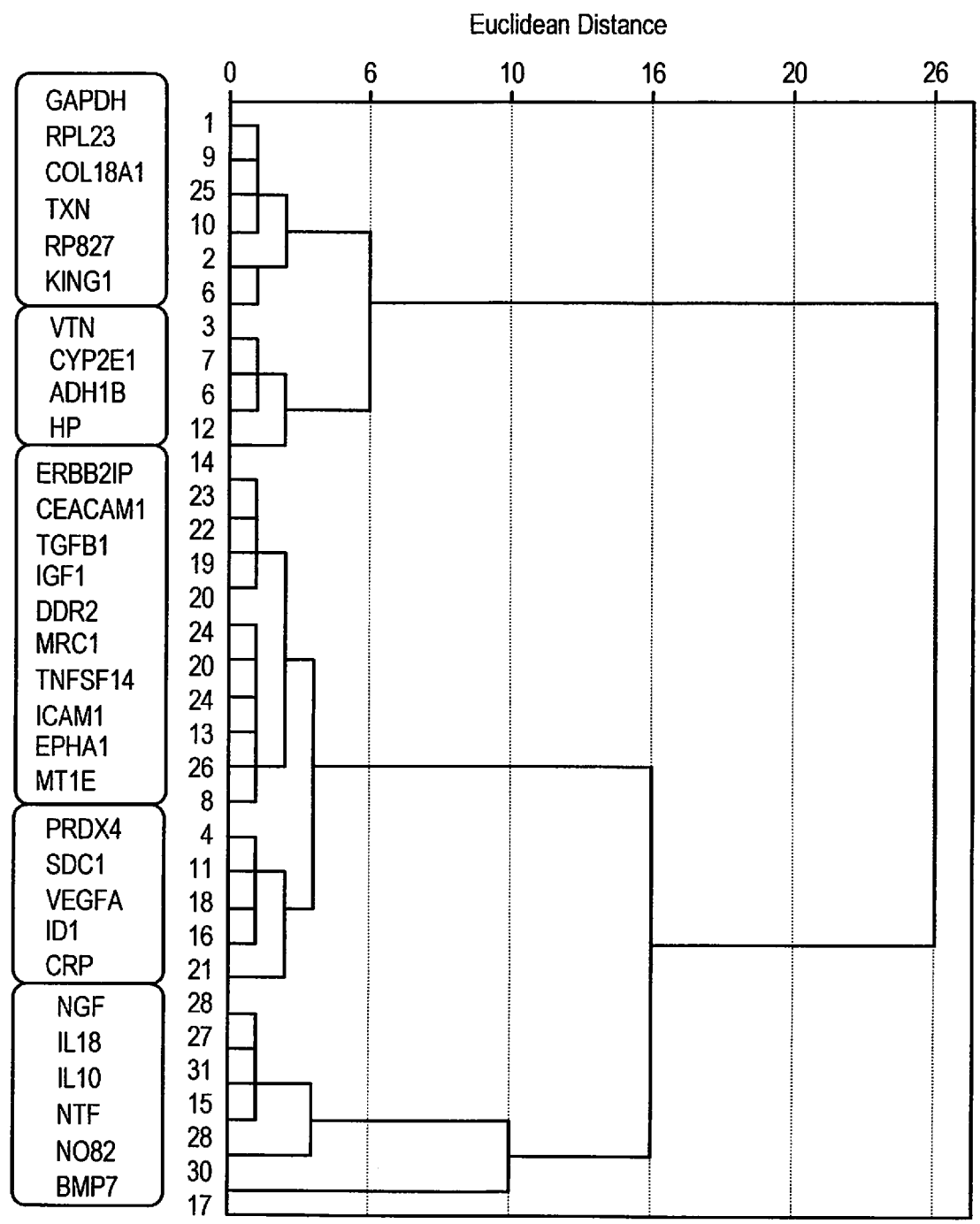
Figure 13D:
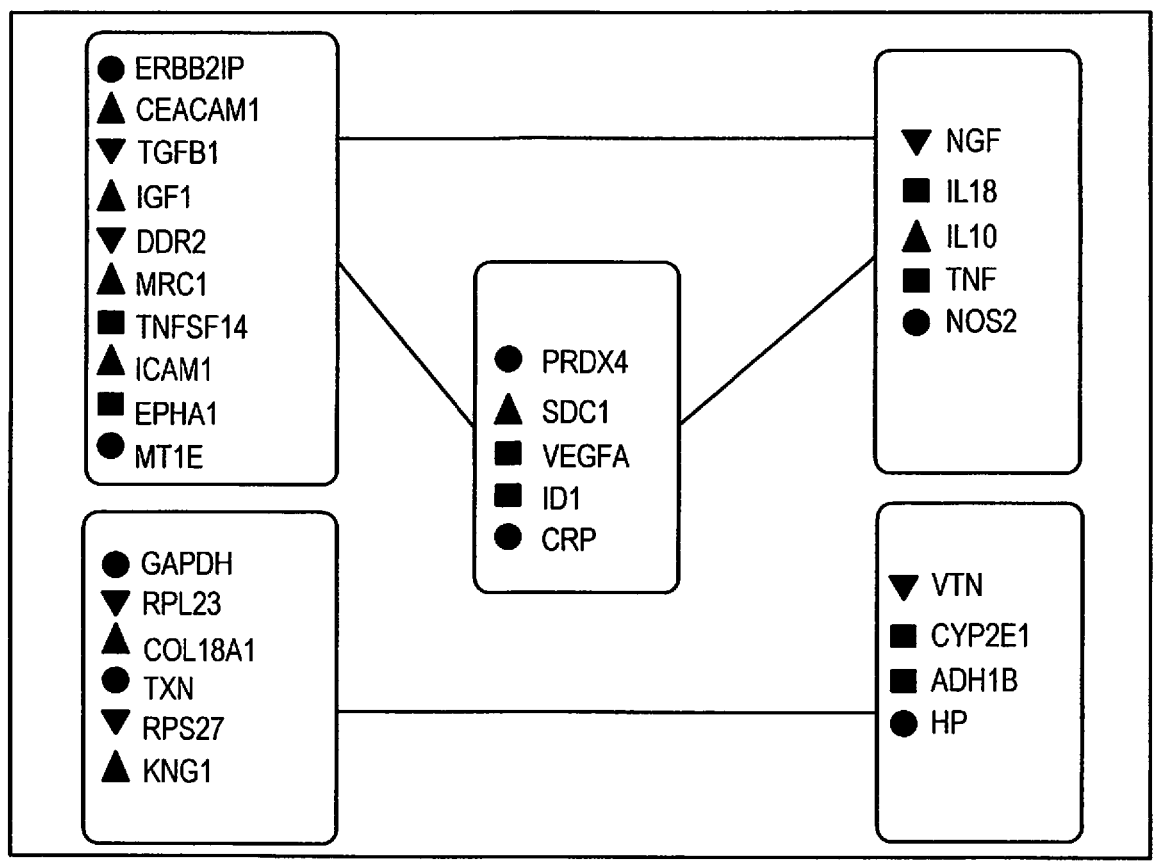

Spearman's correlation analysis was used to study the structure of transcriptional associations among liver prometastatic genes in patients with and without CRC, and to identify those gene correlations changing between patients with and without CRC. As shown in FIG. 12, correlations among genes from patients with CRC were strengthened in the metabolic bioprotection gene group, while they were lost among genes in the immune-regulation gene group. A hierarchical clustering was performed based on Pearson's correlation Euclidean distances among liver prometastatic genes and their gene clusters, and represented as dendrogram plots in order to define the transcriptional structure of prometastatic genes in hepatic biopsies from patients with and without CRC (FIG. 13A and 13C). A cluster including PRX4, SDC1, VEGFA, ID1 and CRP genes defined the main change in the hepatic transcriptional structure between patients with and without CRC (FIG. 13B and 13D). Therefore, an additional feature contributing to identifying CRC-dependent gene expression changes in patients without clinical evidence of CRC is the correlation pattern among liver prometastatic genes.

Figure 4A:
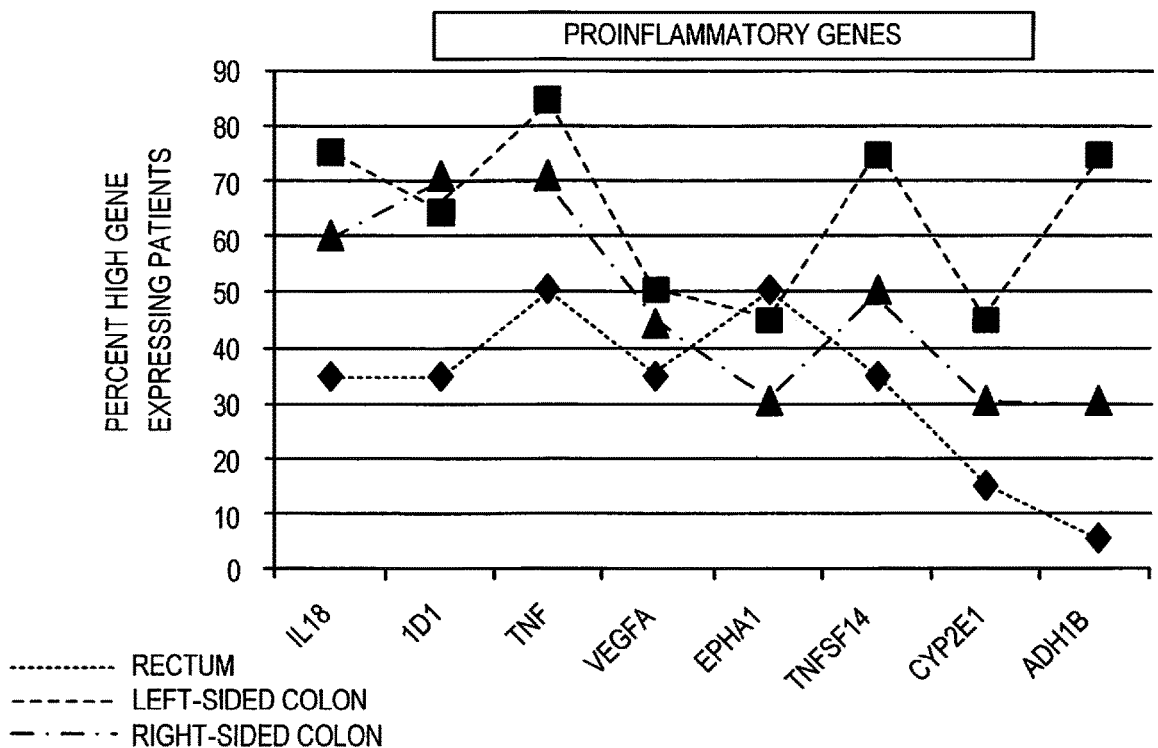
FIGS. 4A-4D respectively show distribution of liver prometastatic gene high-expressing patients by functional categories (proinflammatory, immune-regulation, metabolic Bioprotection and fibrogenic/regeneration) and tumor location in patients with CRC.
Figure 4B:
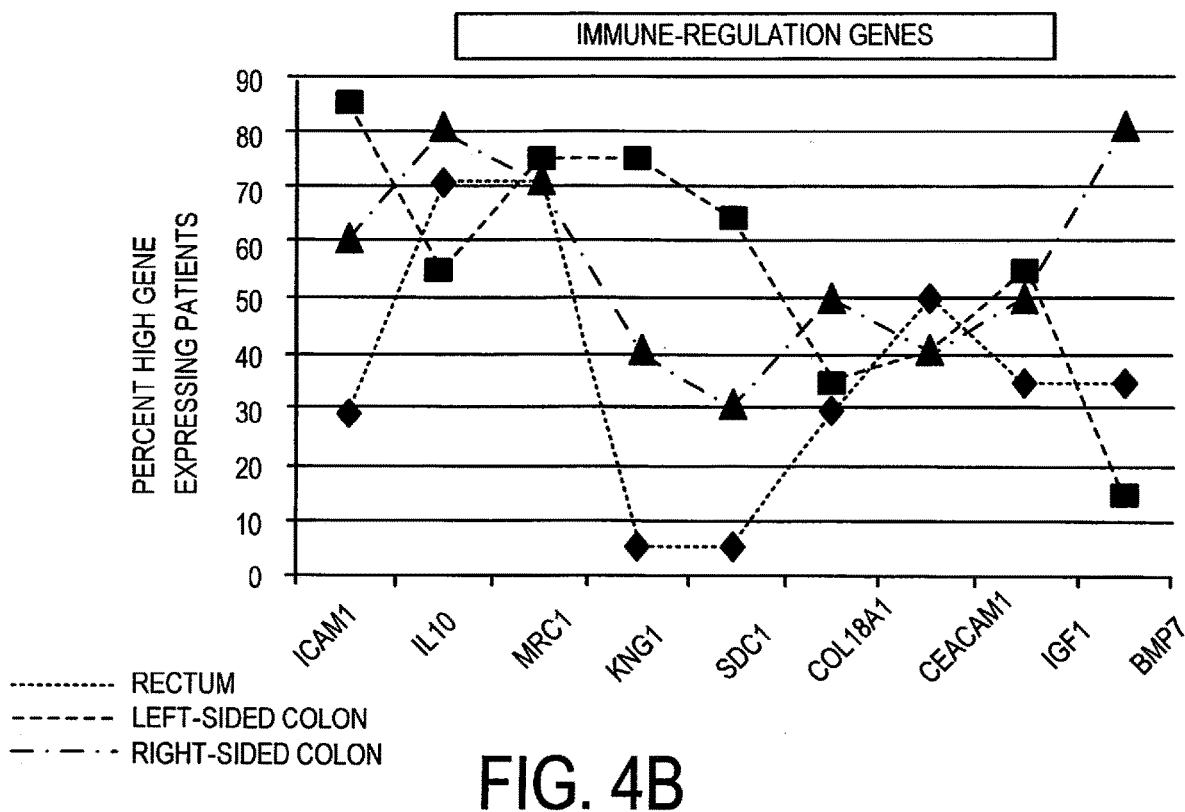
Figure 4C:
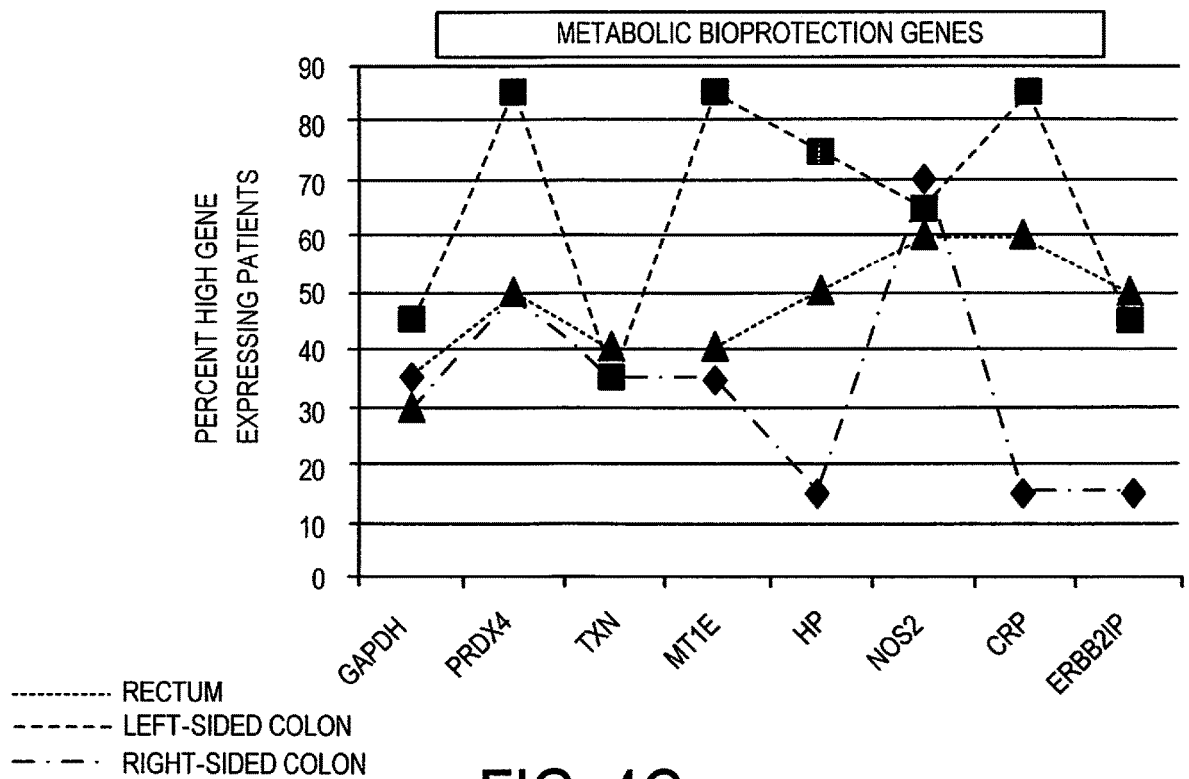
Figure 4D:
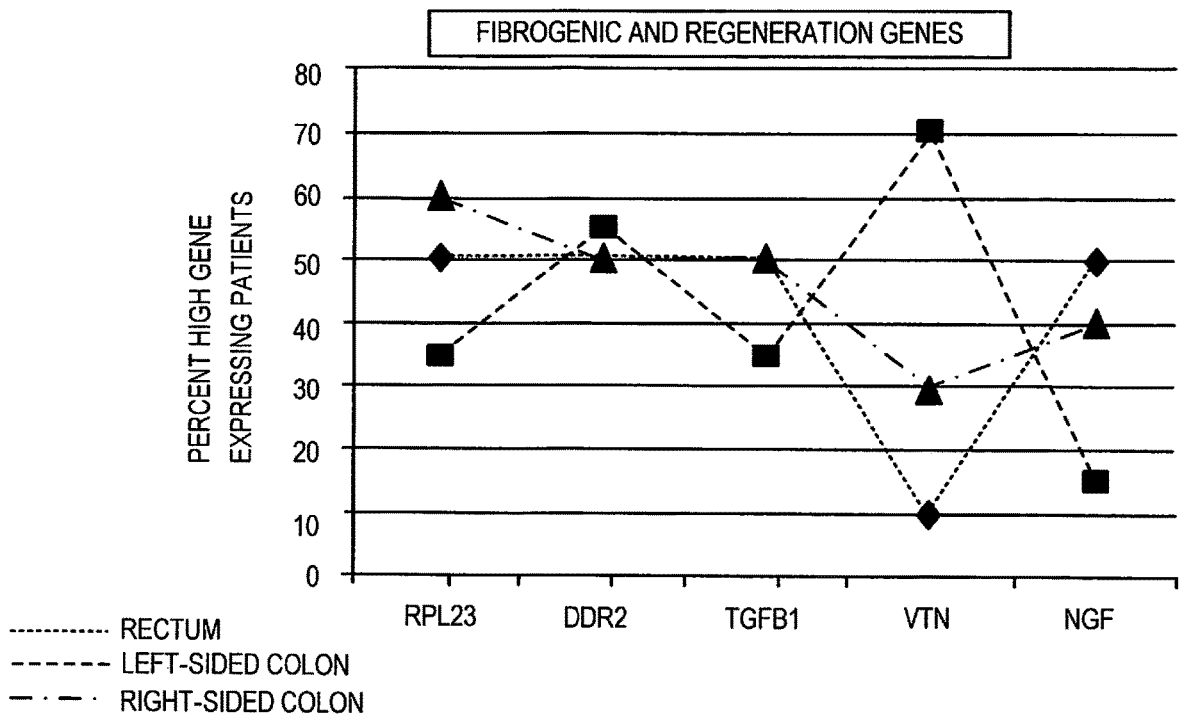
Figure 5A:
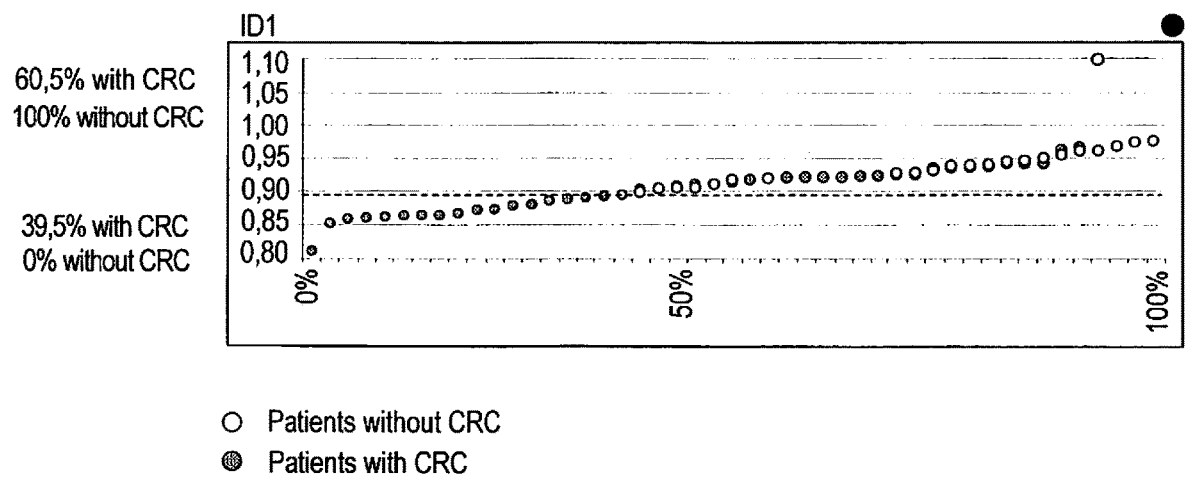
FIGS. 5A-5H show comparisons between proinflammatory gene expression levels in liver from patients with and without CRC.
Figure 5B:
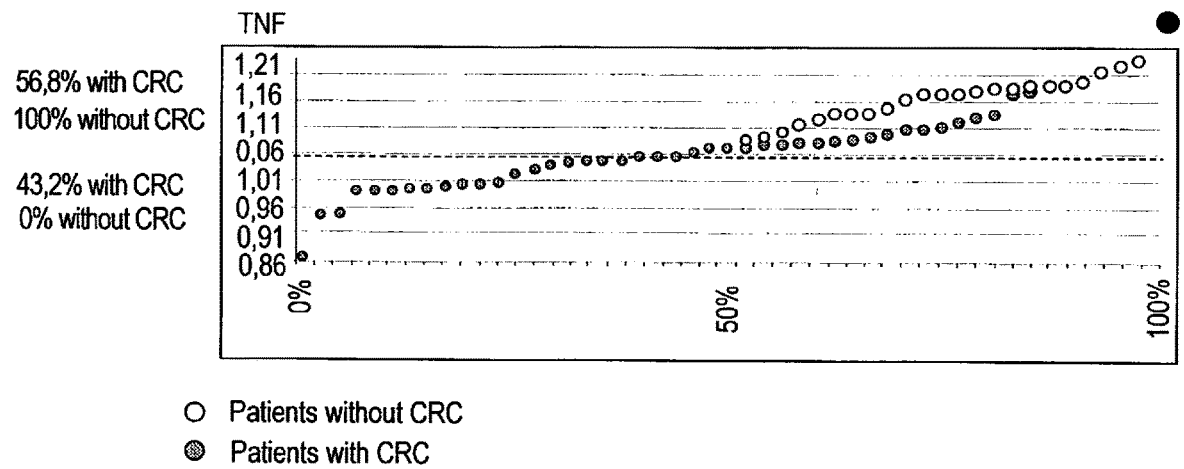
Figure 5C:
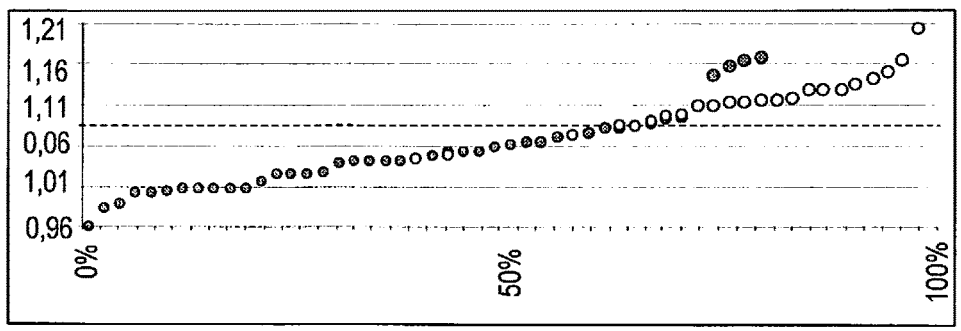
Figure 5D:
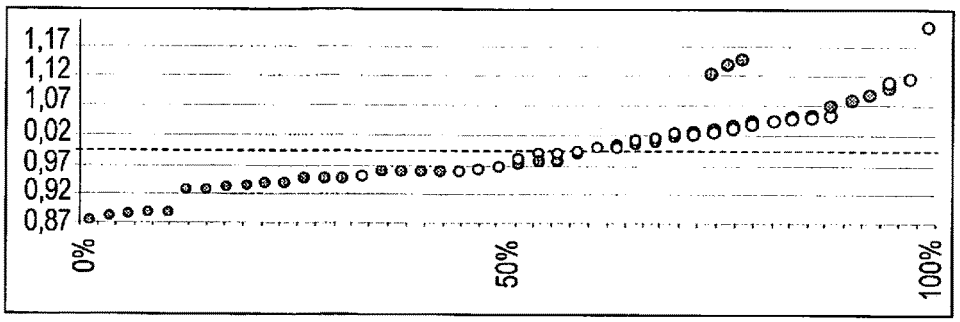
Figure 5E:
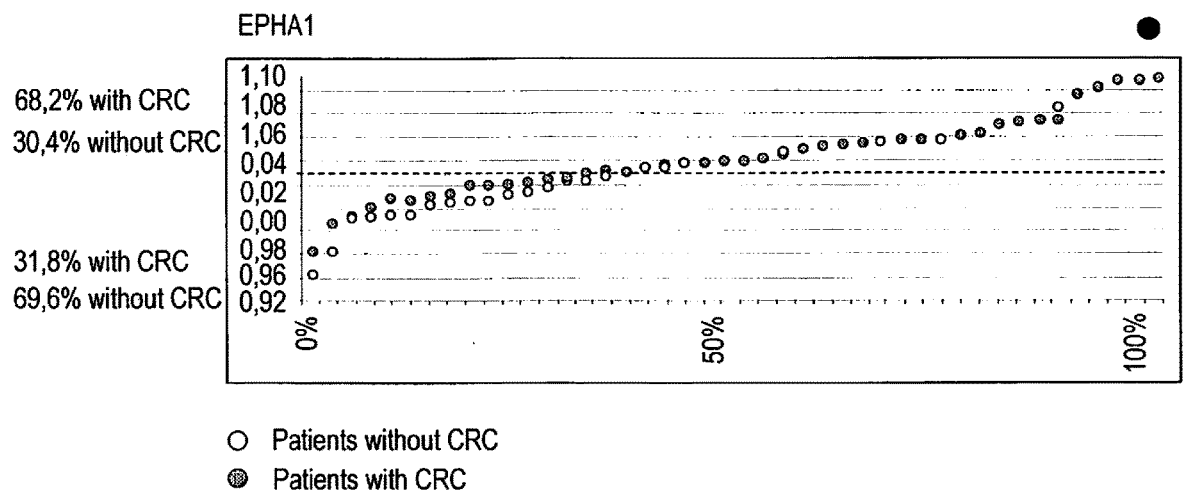
Figure 5F:
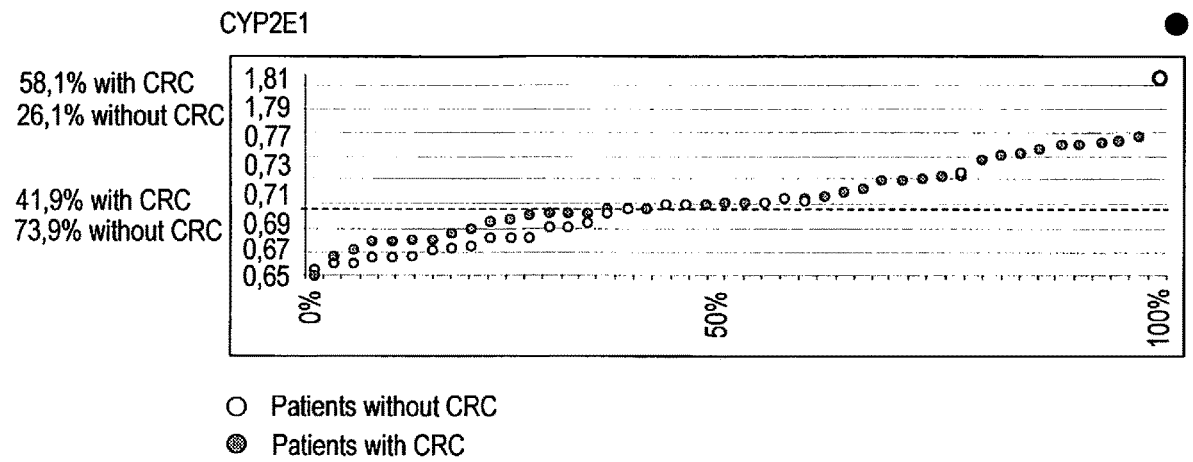
Figure 5G:
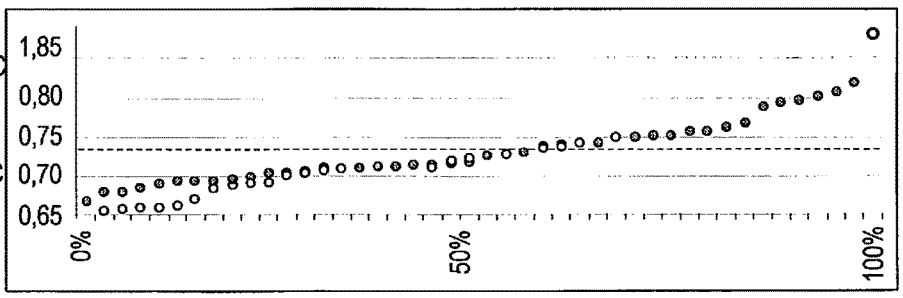
Figure 5H:
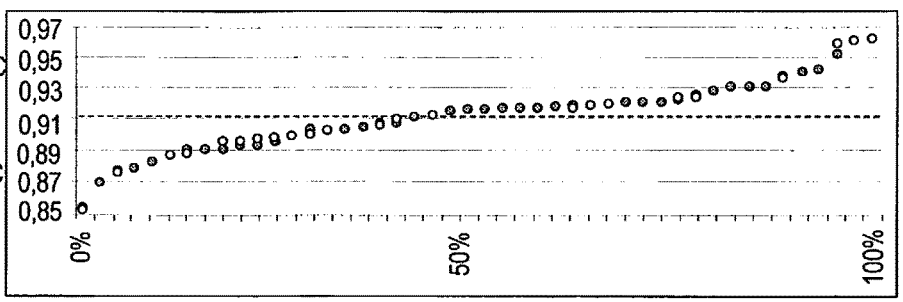
Figure 6A:
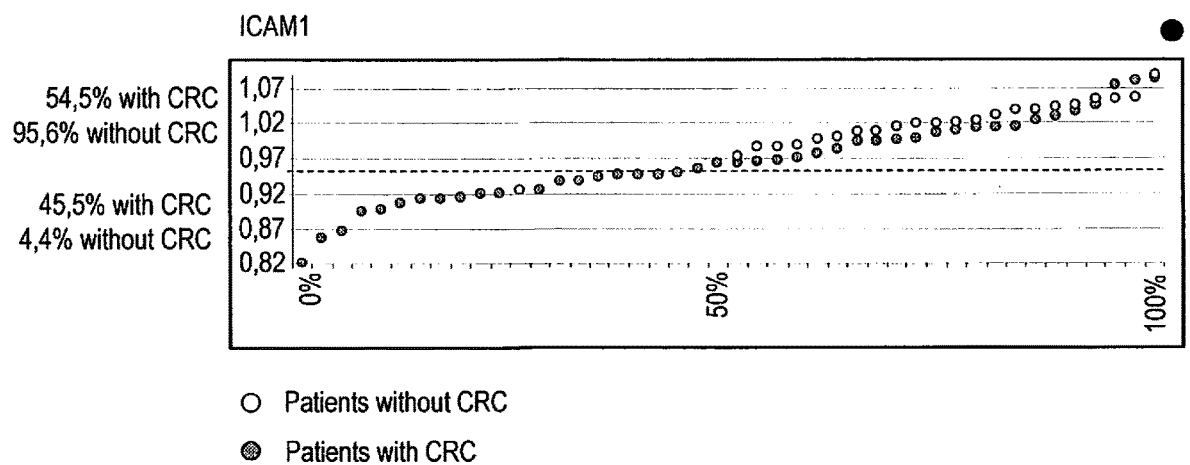
FIGS. 6A-6I show comparisons between immuno-regulation gene expression levels in liver from patients with and without CRC.
Figure 6B:
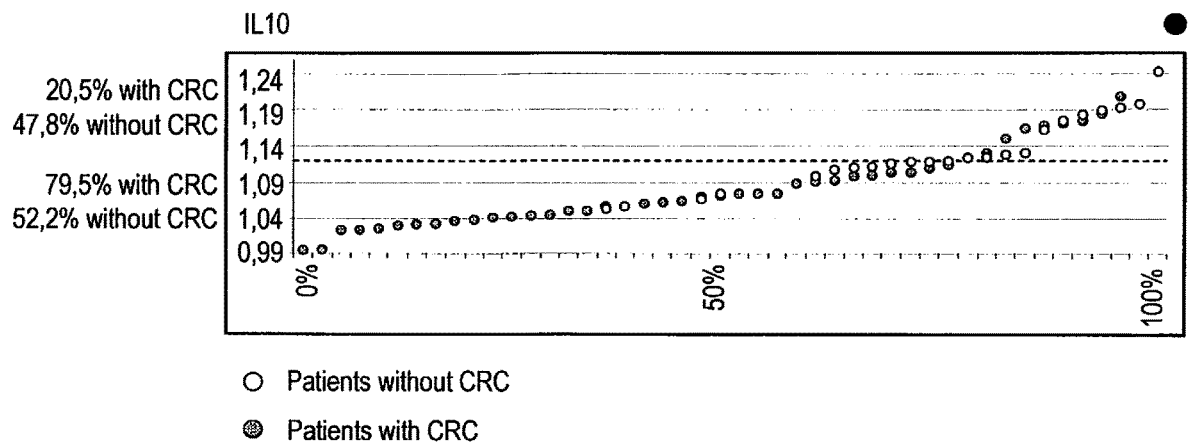
Figure 6C:
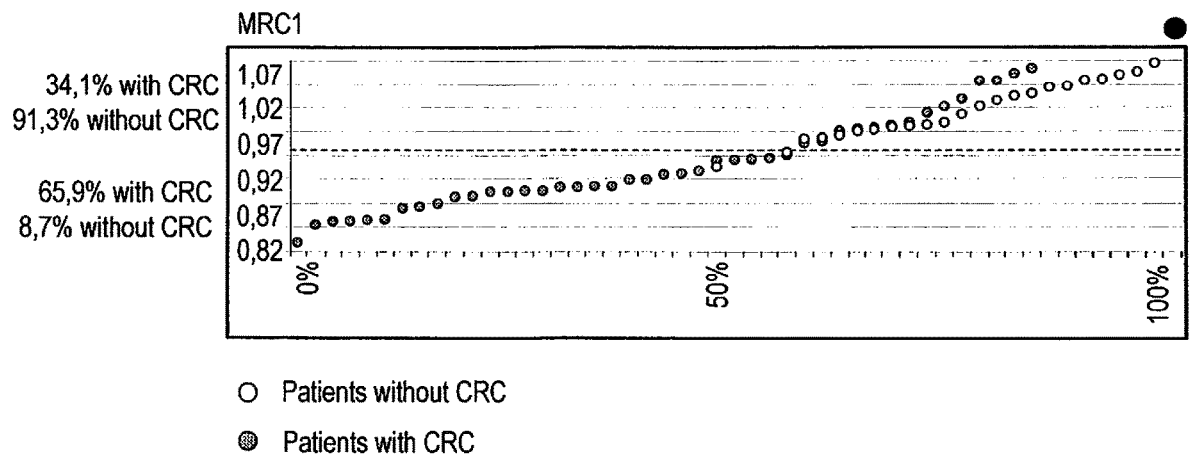
Figure 6D:
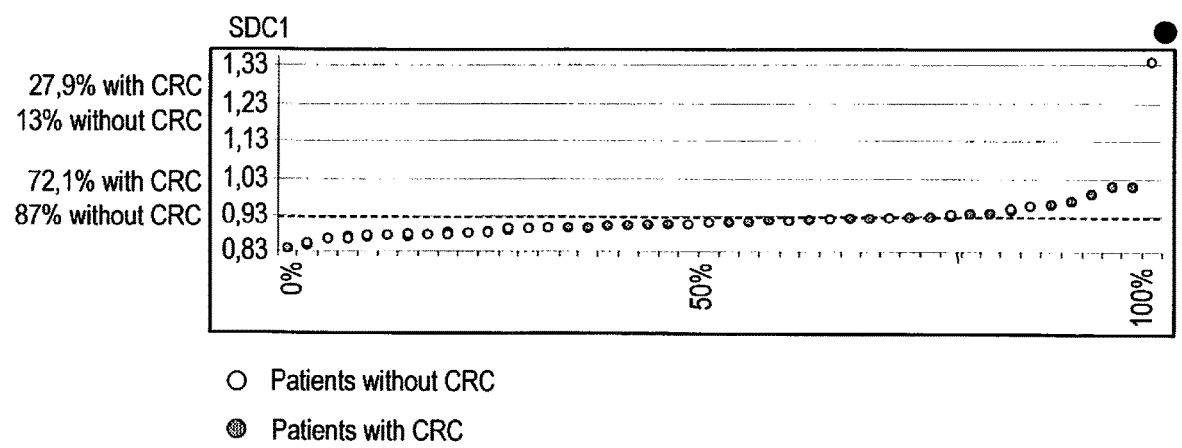
Figure 6E:
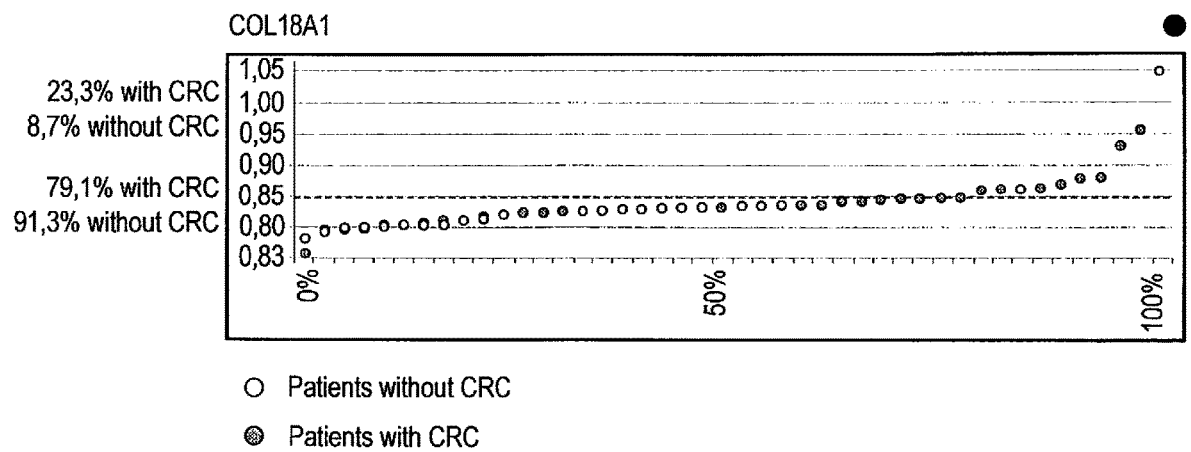
Figure 6F:
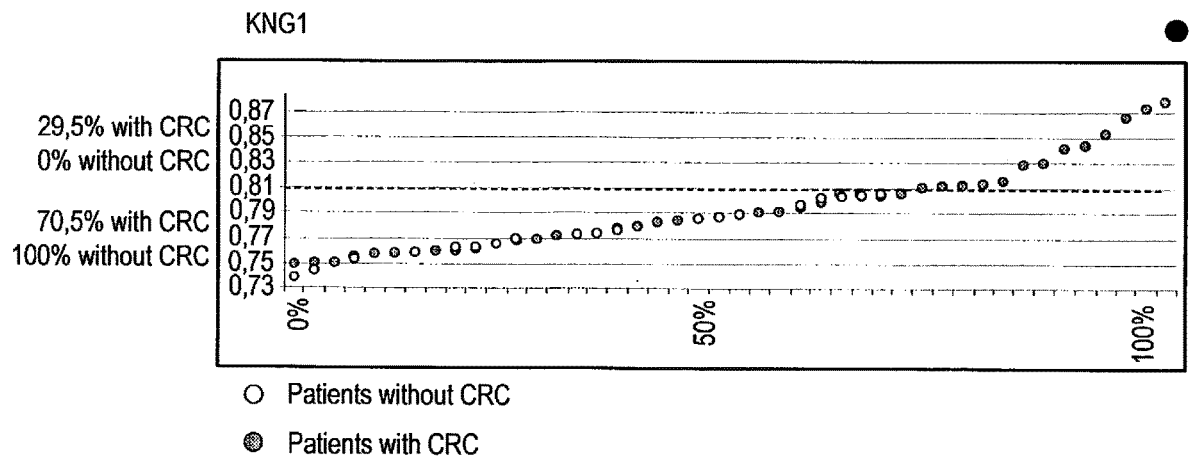
Figure 6G:
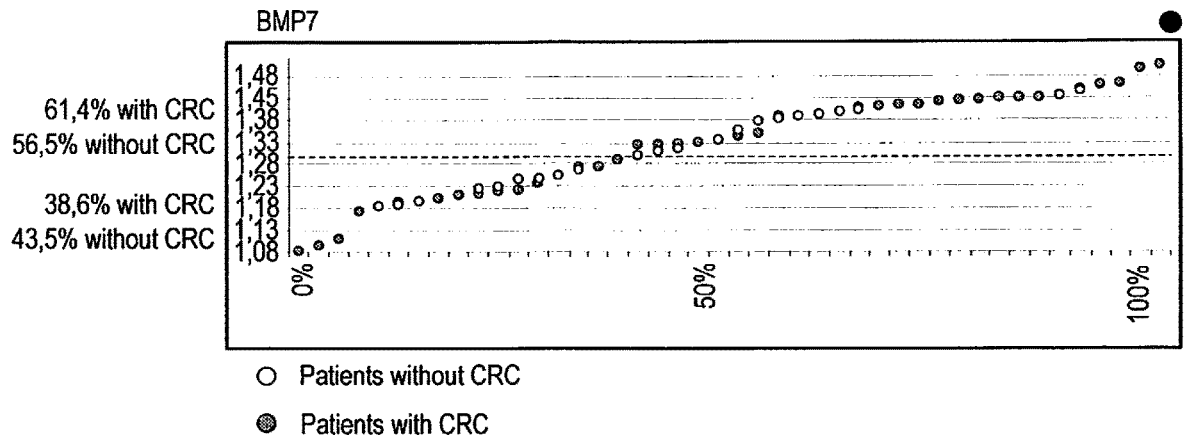
Figure 6H:
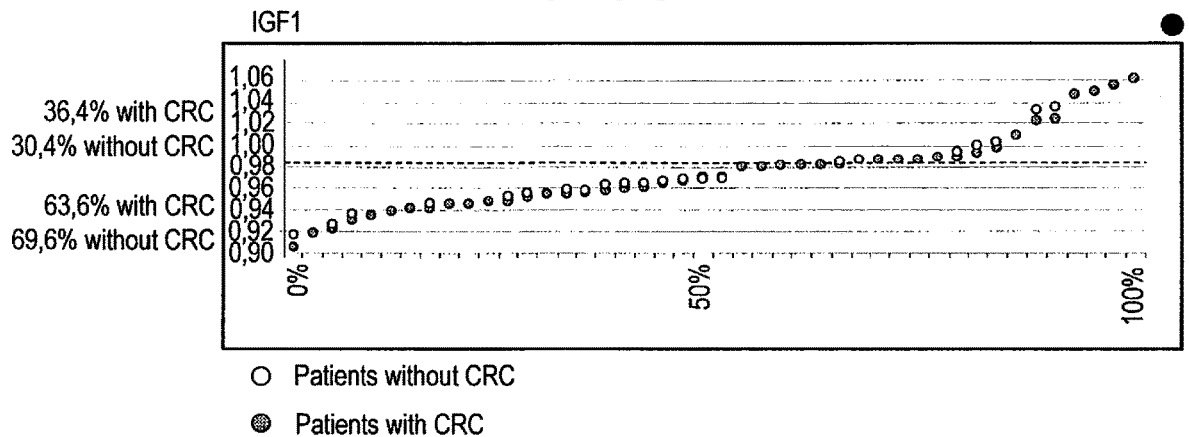
Figure 6I:
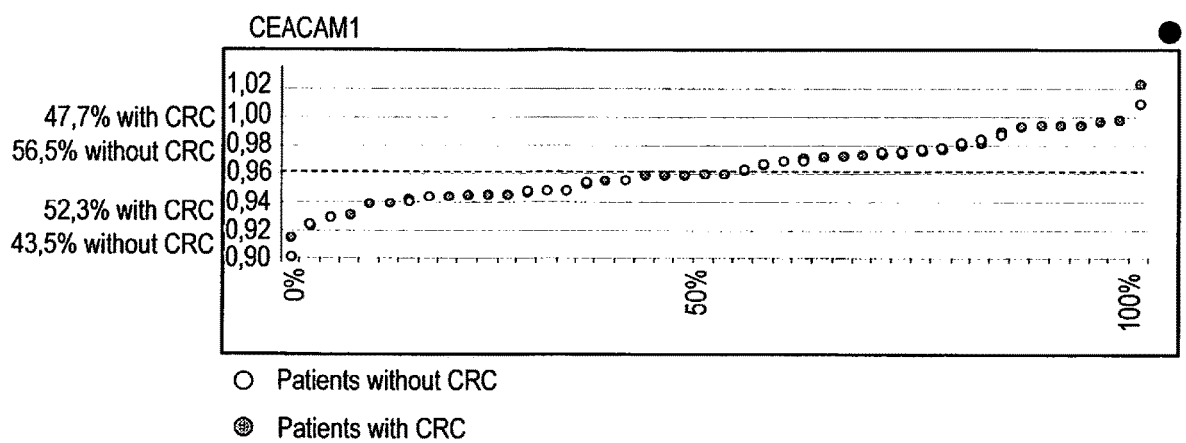
Figure 7A:
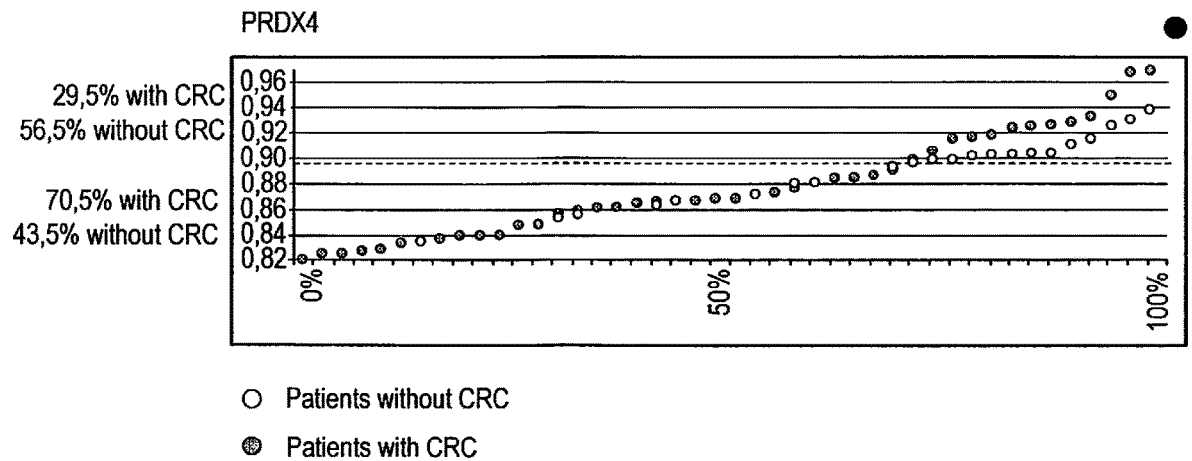
FIGS. 7A-7H show comparisons between metabolic bioprotection gene expression levels in liver from patients with and without CRC.
Figure 7B:
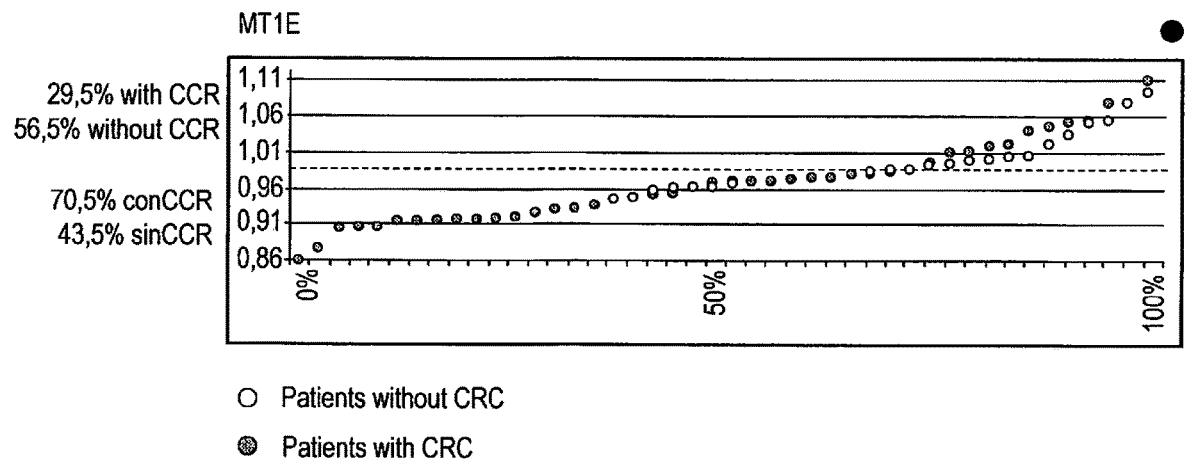
Figure 7C:
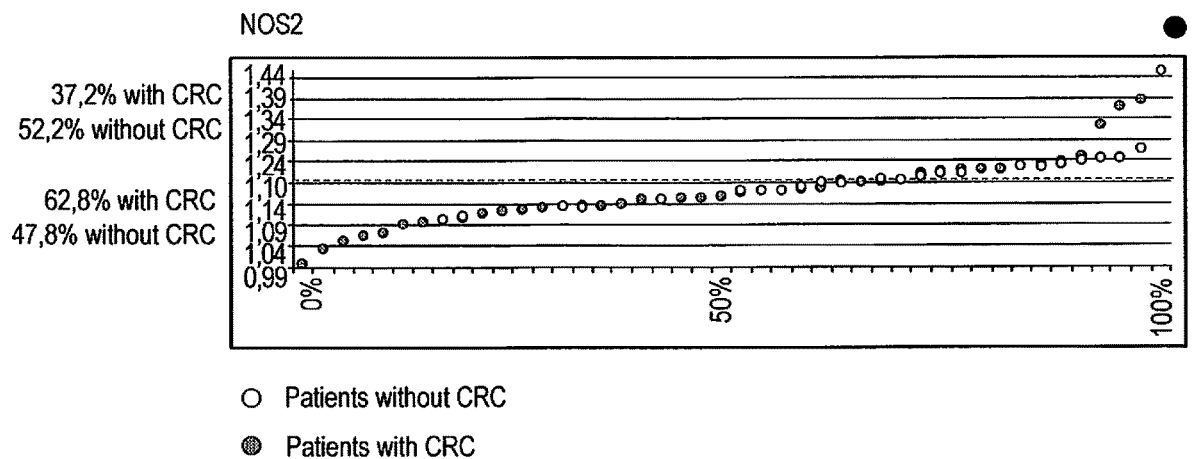
Figure 7D:
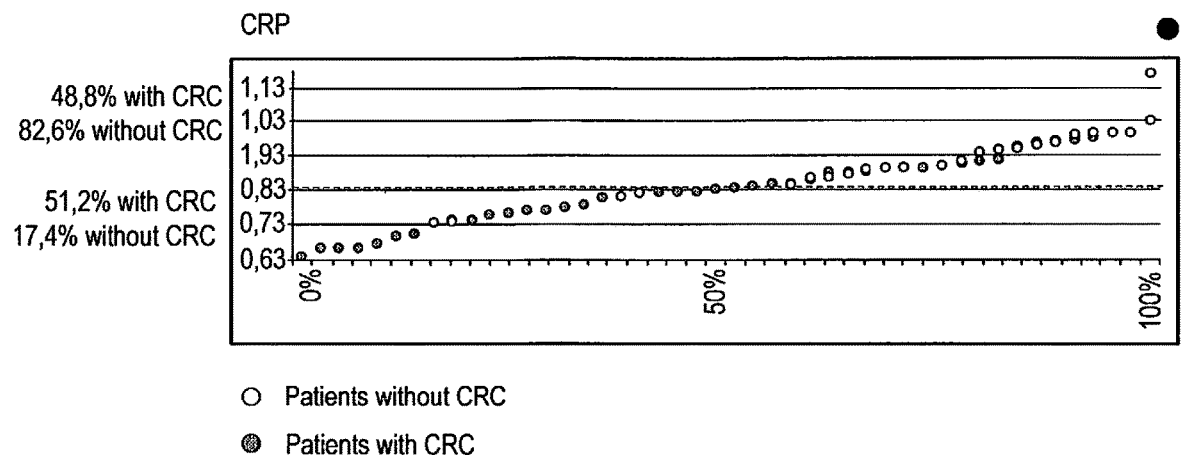
Figure 7E:
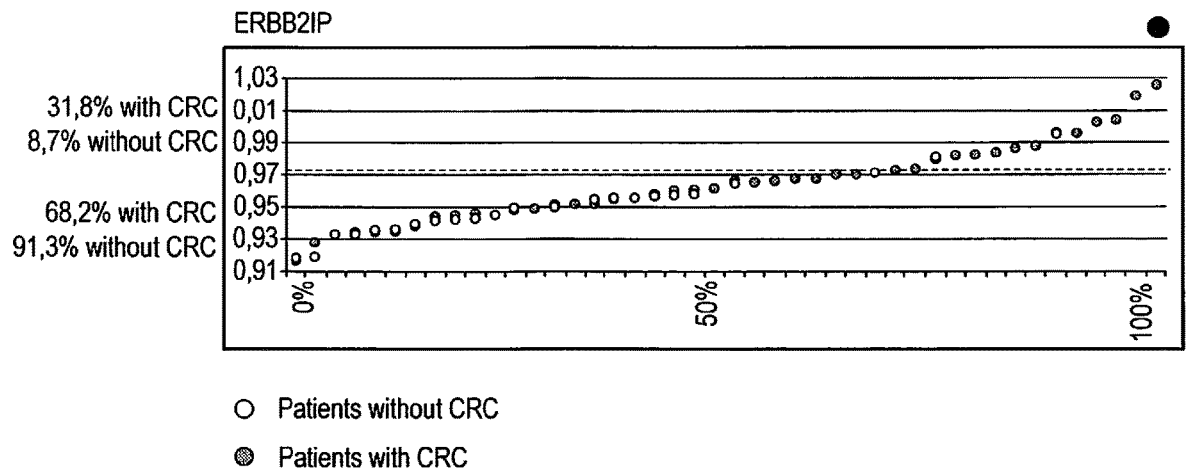
Figure 7F:
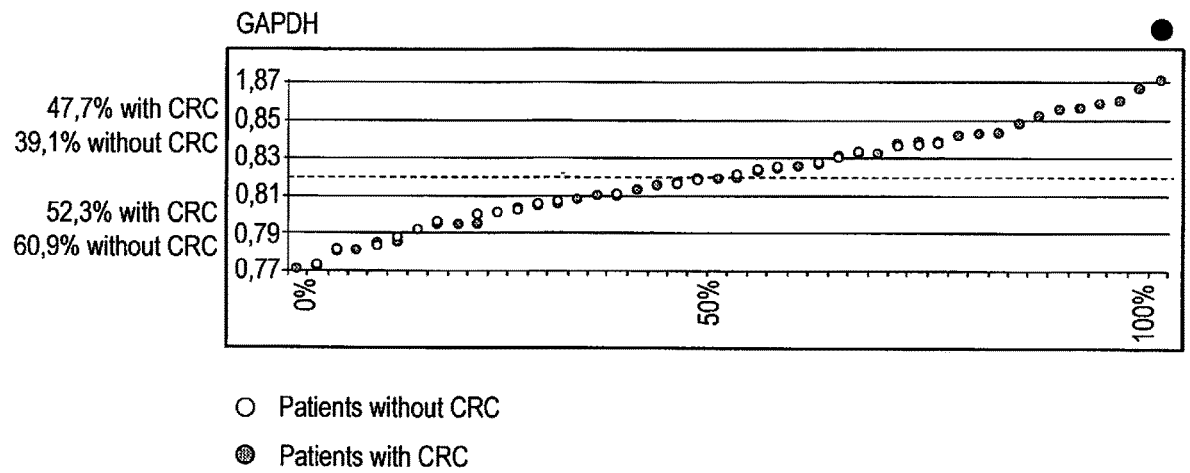
Figure 7G:
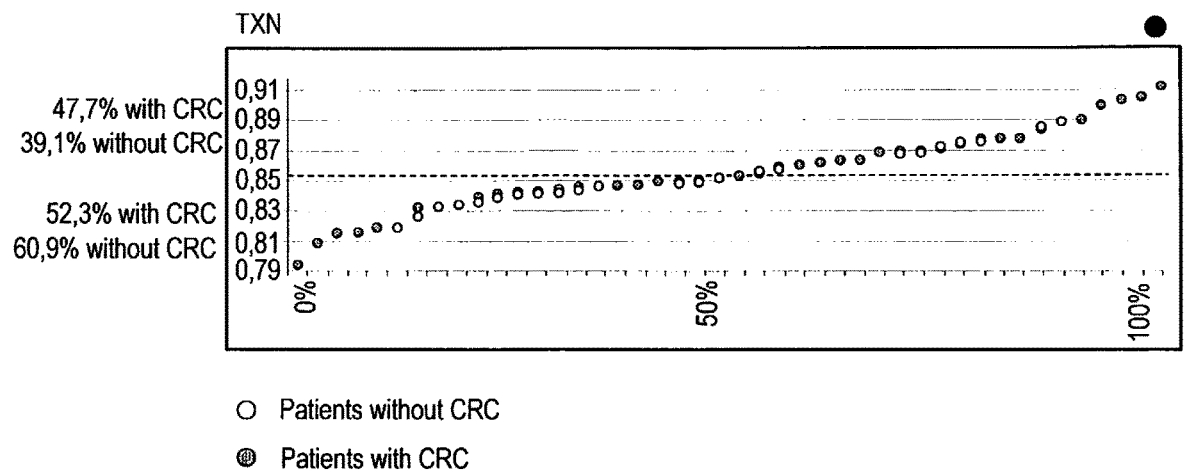
Figure 7H:
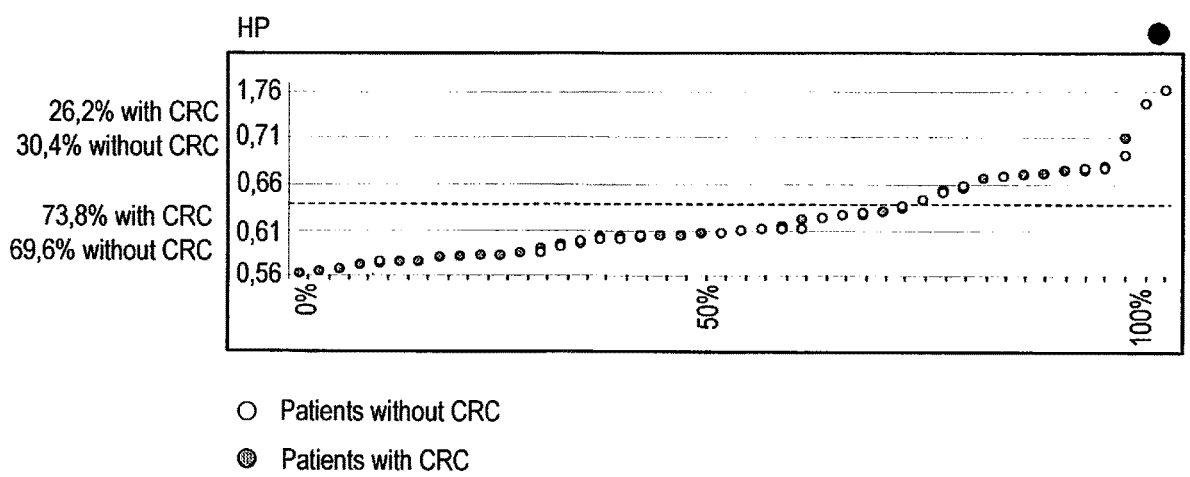
Figure 8A:
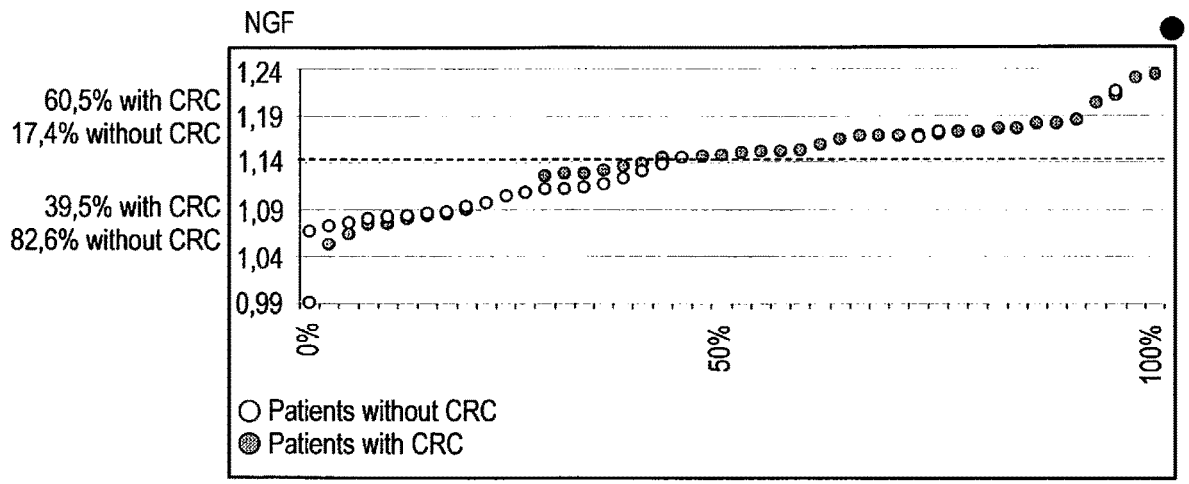
FIGS. 8A-8F show comparisons between Fibrogenic and Regeneration gene expression levels in liver from patients with and without CRC.
Figure 8B:
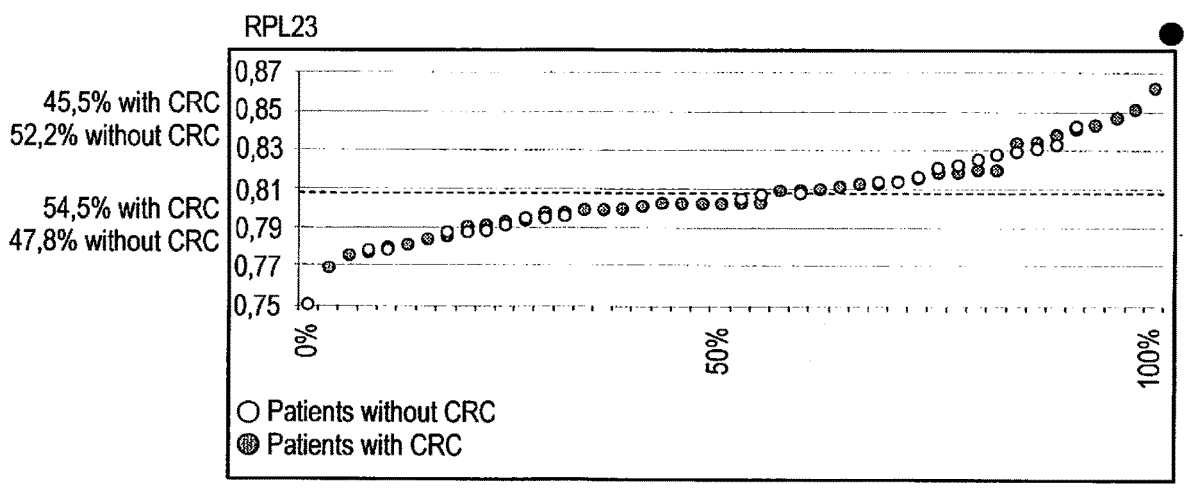
Figure 8C:
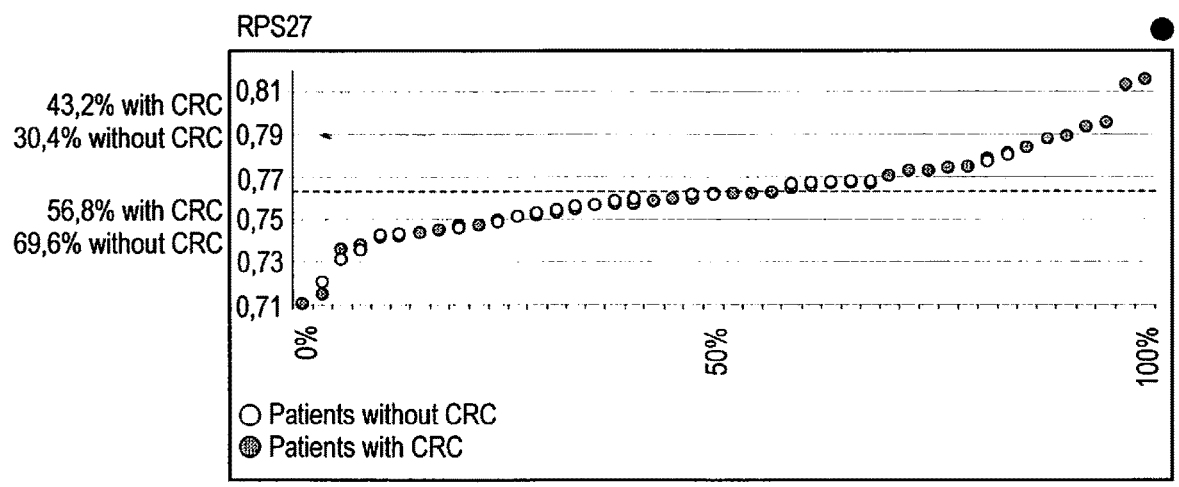
Figure 8D:
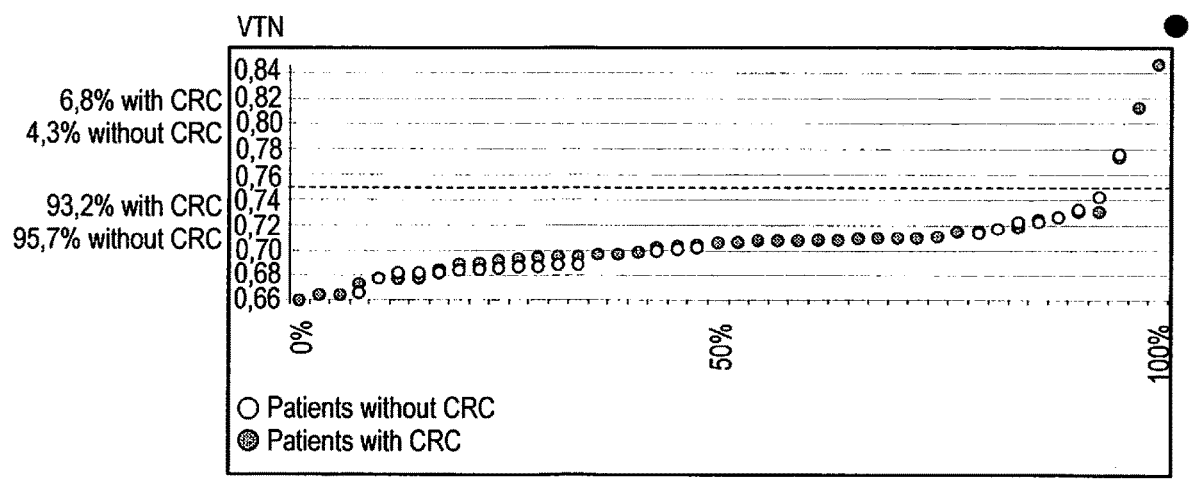
Figure 8E:
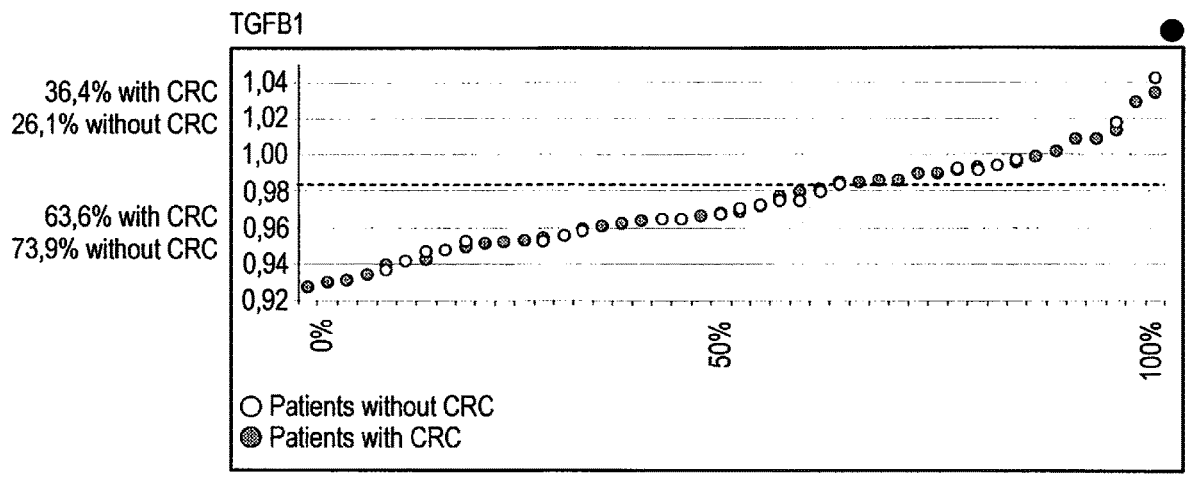
Figure 8F:
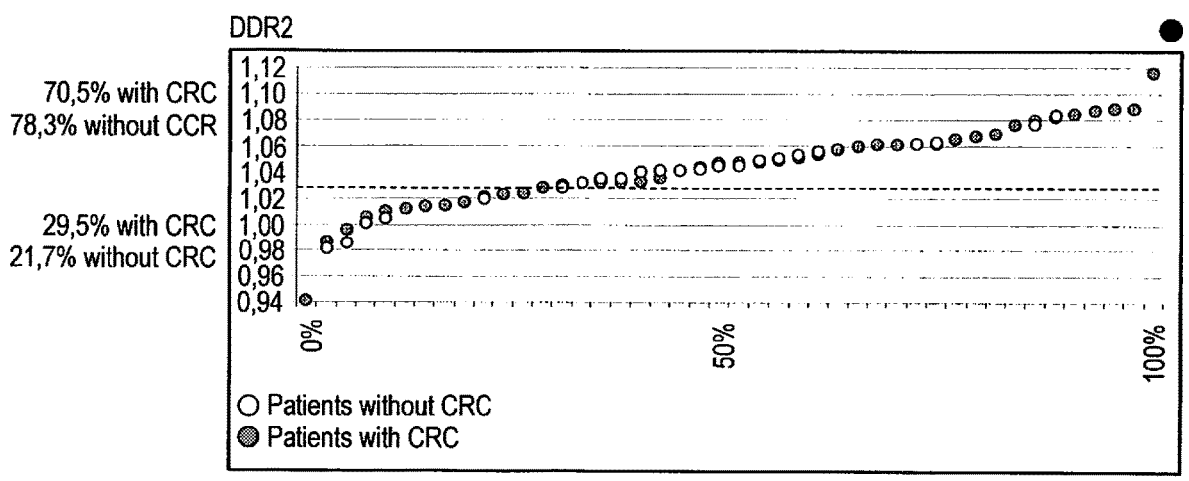

It was also revealed that the relationship between and among gene expression levels within functional categories differ according to location of the primary tumor in patients having CRC cancer. According to another aspect of the present invention, this information may be used to determine or direct a type of treatment administered to a patient. FIGS. 4A, 4B, 4C and 4D, for example, show differences in distributions of liver prometastatic genes in high-expressing patients according to whether the primary tumor is located in the rectum (doted trace), right-side (dot-dash trace) colon and left-side (dashed trace) colon. In particular, FIG. 4A shows a first relational distribution of liver prometastatic gene expressions in high-expressing patients for Proinflammatory genes (IL18, ID1, TNF, VEFA, EPHA1, TSFSFI4, CYP2E1 and ADH1B) according to primary tumor location in patients with CRC. FIG. 4B shows a second relational distribution of liver prometastatic gene expressions in high-expressing patients for Immune regulation genes (ICAM1, IL10, MRC1, KNG1, SDI1, COL18A1, IGF1 and MP 7) according to primary tumor location in patients with CRC. FIG. 4C shows a third relational distribution of liver prometastatic gene expressions in high-expressing patients for Metabolic Bioprotection genes (GAPDH, PRDX4, TXN, MT1E, HP, NOS2, CRP, and ERBB2IP) according to primary tumor location in patients with CRC. FIG. 4D shows a fourth relational distribution of liver prometastatic gene expressions in high-expressing patients for Fibrogenic/Regeneration genes (RPL23, DDR2, TGFB1, VTN and NGF) according to primary tumor location in patients with CRC.

A further aspect of the invention includes a complementary diagnostic test to indicate a possible anatomical location of an occult CRC in patients without clinical evidence of CRC, but with other digestive system diseases increasing CRC risk, such as cholelithiasis and metabolic syndrome. As shown in FIGS. 13A-13D and 4A-4D, patients with tumors of localization in the left-side colonic area (including splenic flexure, descending colon, sigmoid colon or recto sigmoid junction) were the ones that most frequently increased the expression of liver prometastatic genes, followed by patients with right-sided tumors (including cecum, ascending colon, hepatic flexure or transverse colon), whereas patients with rectal tumors were those more frequently decreasing it. The anatomical location of CRC determined the liver prometastatic gene expression pattern and the percentage of patients with high and low expression of these genes. Therefore, in accordance with this further aspect of the invention, these patterns suggest the possible anatomical location of an occult CRC in patients without clinical evidence of CRC, but with other digestive system diseases increasing CRC risk, such as cholelithiasis and metabolic syndrome in order to provide a basis to direct and determine a best possible treatment regime. Again, a rule-based processing system to receive data inputs and appropriate program instructions may be utilized to automatically output this determination on a display device or other output.

The Table of FIG. 4A-4D (Table 6) shows distribution of liver prometastatic genes by functional categories and tumor location. Rectal Tumor Pattern is indicate by Low hepatic expression of genes from the four prometastatic gene functional categories with high-IL10, MRC1 and NOS2 gene expression, which suggest Immunotolerance/immunosuppression without inflammatory background and possible beneficial effects of immunotherapy in metastasis prevention. Left-sided colonic Tumor Pattern (including CRC within the splenic flexure, descending colon, sigmoid colon or recto sigmoid junction) is indicated by High hepatic expression of proinflammatory, immune regulation and metabolic bioprotection genes, with drop in BMP7 and NGF gene expression, which suggests very high-risk prometastatic microenvironment and possible beneficial effects of anti-inflammatory therapies in metastasis prevention. Right-sided colonic Tumor Pattern (including primary CRC in the cecum, ascending colon, hepatic flexure or transverse colon) is indicated by a Slight increase of proinflammatory and immune regulation gene expression with ADH1B, SDC1 and VT gene expression decrease, which suggests slight immunotolerance/immunosuppression under inflammatory conditions and possible beneficial effect of anti-inflammatory therapies in metastasis prevention. According to yet another aspect of the present invention, an analytical determination may be made to determine a treatment regime in accordance with high-low gene expression levels of genes within respective functional categories and anatomic location of the tumor along the colonic tract. A processing device also may be utilized to provide such determination in an automated diagnostic and treatment system.

A yet further aspect of the invention includes personalized treatment of patients based on a multiplex of molecular biomarkers defining precise functional features of cancer that may strongly increase the efficacy of the chosen therapies. In this study, the analysis of liver prometastatic gene functional categories by anatomical location of the CRC identified three distinct functional patterns with therapeutic implications (Table 6 of FIG. 4). Rectal Tumor Pattern was indicated by Low hepatic expression of genes from the four prometastatic gene functional categories with high-IL10, MRC1 and NOS2 gene expression, which suggest Immunotolerance/immunosuppression without inflammatory background and possible beneficial effects of immunotherapy in metastasis prevention. Left-sided colonic Tumor Pattern is indicated by High hepatic expression of proinflammatory, immune regulation and metabolic bioprotection genes, with drop in BMP7 and NGF gene expression, which suggests very high-risk prometastatic microenvironment and possible beneficial effects of anti-inflammatory therapies in metastasis prevention. Right-sided colonic Tumor Pattern was indicated by Slight increase of proinflammatory and immune regulation gene expression with ADH1B, SDC1 and VT gene expression decrease, which suggests slight Immunotolerance/immunosuppression under inflammatory conditions and possible beneficial effect of anti-inflammatory therapies in metastasis prevention.

The written description, drawing figures and charts presented herein are not intended to limit the scope of the invention but merely provide an illustration of the core concepts and embodiments that may be implemented to carry out the teachings set forth herein. Based on these teachings, persons skilled in the art may devise alternative embodiments or modify the illustrated embodiments. Accordingly, the scope of invention is defined by the appended claims rather than the illustrated embodiments.

References

Anasagasti M J, Alvarez A, Mendoza L, Martin J J y Vidal-Vanaclocha F. Sinusoidal endothelium release of hydrogen peroxide enhances VLA-4 mediated melanoma cell adherence and tumor cytotoxicity during interleukin-1 promotion of melanoma hepatic metastasis. Hepatology 25:840-846 (1997).

Anasagasti M J, Martin J J, Mendoza L, Obrador E, Estrela J M, McCuskey R S, and Vidal-Vanaclocha F. Glutathione protects metastatic melanoma cells against oxidative stress in the murine hepatic microvasculature. Hepatology 27: 1249-1256 (1998).

Anasagasti M J, Olaso E, Calvo F, Martin J J, Mendoza M, Bidaurrazaga J, and Vidal-Vanaclocha F. Interleukin-1 (IL-1)-Dependent and -Independent Mouse Melanoma Metastases. J Natl Cancer Institute 89:645-651 (1997).

Aoyama T, Kashiwabara K, Oba K, Honda M, Sadahiro S, Hamada C, Maeda H, Mayanagi S, Kanda M, Sakamoto J, Saji S, Yoshikawa T. Clinical impact of tumor location on the colon cancer survival and recurrence: analyses of pooled data from three large phase III randomized clinical trials. Cancer Med. 2017 Sep. 25. doi: 10.1002/cam4.1208.

Arteta B, Lasuen N, Sveinbjornssøn B, Smedsrød B and Vidal-Vanaclocha F. Murine Colon Carcinoma Cell interaction with Liver Sinusoidal Endothelium Inhibits Anti-Tumor Immunity via IL-1 Induced Mannose Receptor. Hepatology 2010; 51: 2172-2182.

Arteta B, Lasuen N, Sveinbjornssøn B, Smedsrød B and Vidal-Vanaclocha F. Murine Colon Carcinoma Cell interaction with Liver Sinusoidal Endothelium Inhibits Anti-Tumor Immunity via IL-1 Induced Mannose Receptor. Hepatology 2010; 51: 2172-2182.

Badiola I, Olaso E, Crende O, Friedman S L, Vidal-Vanaclocha F. Discoidin domain receptor 2 deficiency predisposes hepatic tissue to colon carcinoma metastasis. Gut. 2012 Oct.;61(10):1465-72.

Badiola I, Olaso E, Crende O, Friedman S L, Vidal-Vanaclocha F. Discoidin domain receptor 2 deficiency predisposes hepatic tissue to colon carcinoma metastasis. Gut. 2012 Oct;61(10):1465-72.

Barbois S, Arvieux C, Leroy V, Reche F, Stürm N, Borel A L. Benefit-risk of intraoperative liver biopsy during bariatric surgery: review and perspectives. Surg Obes Relat Dis. 2017 Aug. 14. pii: S1550-7289(17)30359-3.

Beaskoetxea J ; Ruiz-Casares E; Telleria N; del Villar A; Garcia de Durango C; Lapuente F; Gil A; Fernandez-Nespral V; Ielpo B; Carusso R; Duran H; Quijano Y; de Vicente E; Vidal-Vanaclocha F. Liver metastasis-Associated colon cancer cell genes: microenvironmental regulation and therapeutic implications. J Hepatology (in preparation).

Carrascal T, Mendoza L, Vacarcel M, Salado C, Egilegor E, Telleria N, Vidal-Vanaclocha F and Dinarello C A. Interleukin/18 binding protein reduces B16 Melanoma Hepatic Metastasis by neutralizing the adhesiveness and growth factors of sinusoidal endothelial cell. Cancer Res 63:491-7 (2003).

Crende O, Sabatino M, Valcarcel M, Carrascal T, Riestra P, Lopez-Guerrero J A, Nagore E, Mandruzzato S, Wang E, Marincola F M, Vidal-Vanaclocha F. Metastatic lesions with and without interleukin-18-dependent genes in advanced-stage melanoma patients. Am J Pathol. 2013 Jul.; 183(1): 69-82.

Garcia de Durango C, Marina Perez-Gordo; Eva Ruiz Casares, and Fernando Vidal-Vanaclocha. Transcriptional Association of Bacterial Endotoxin-Dependent Colorectal Cancer Cell Soluble Proteins to Hepatic Prometastatic Signature Genes. Gastroenterology (in preparation).

Garcia De Durango Cr, De Wit M, Piersma Sr, Knol J, Pham Tv, Pérez-Gordo M, Fijneman Rja, Vidal-Vanaclocha F, Jimenez Cr. Lipopolysaccharide-regulated secretion of soluble and vesicle-based colorectal cancer cell proteins. J Proteomics 2017 (in preparation).

Gil A; Garcia de Durango C; Lapuente F; Fernandez-Nespral V; Ielpo B; Carusso R; Duran H; Quijano Y; de Vicente E; Vidal-Vanaclocha F. Pathophysiological anthropometric correlations of liver prometastatic genes in patients with primary colorectal cancer. Am J Pathol (in preparation).

Gosavi S, Mishra R R, Kumar V P. Study on the Relation between Colorectal Cancer and Gall Bladder Disease. J Clin Diagn Res. 2017 Mar.; 11(3):OC25-OC27.

Lee T, Yun K E, Chang Y, Ryu S, Park D I, Choi K, Jung Y S. Risk of Colorectal Neoplasia According to Fatty Liver Severity and Presence of Gall Bladder Polyps. Dig Dis Sci. 2016 Jan;61(1):317-24.

Marquez J, Kohli M, Arteta B, Chang S, Li W B, Goldblatt M, Vidal-Vanaclocha F. Identification of hepatic microvascular adhesion-related genes of human colon cancer cells using random homozygous gene perturbation. Int J Cancer. 2013 Nov.;133(9):2113-22.

Marquez J, Kohli M, Arteta B, Chang S, Li W B, Goldblatt M, Vidal-Vanaclocha F. Identification of hepatic microvascular adhesion-related genes of human colon cancer cells using random homozygous gene perturbation. Int J Cancer. 2013 Nov.; 133(9):2113-22.

Marshall J C, Collins J W, Nakayama J, Horak C E, Liewehr D J, Steinberg S M, Albaugh M, Vidal-Vanaclocha F, Palmieri D, Barbier M, Murone M, Steeg P S. Effect of inhibition of the lysophosphatidic acid receptor 1 on metastasis and metastatic dormancy in breast cancer. J Natl Cancer Inst. 2012 Sep. 5;104(17):130-19.

Mendoza L, Carrascal T, De Luca M, Fuentes A M, Salado C, Blanco J, Vidal-Vanaclocha F. Hydrogen peroxide mediates vascular cell adhesion molecule-1 expression from interleukin-18-activated hepatic sinusoidal endothelium: implications for circulating cancer cell arrest in the murine liver. Hepatology 34:298-310 (2001).

Mendoza L, Valcarcel M, Carrascal T, Egilegor E, Salado C, Sim B K, Vidal-Vanaclocha F. Inhibition of cytokine-induced microvascular arrest of tumor cells by recombinant endostatin prevents experimental hepatic melanoma metastasis. Cancer Res 64: 304-10 (2004).

Olaso E, Salado C, Gutierrez V, and Vidal-Vanaclocha F. Proangiogenic Role of Tumor-Activated Hepatic Stellate Cells in Melanoma Metastasis. Hepatology 37:674-85 (2003).

Olaso E, Santisteban A, Bidaurrazaga J, Gressner A M, Rosenbaum J, and Vidal-Vanaclocha F. Tumor-dependent activation of hepatic stellate cells during experimental melanoma metastasis. Hepatology 26: 634-642 (1997).

Ruiz-Casares E; Lapuente F; Ielpo B; Carusso R; Duran H; Quijano Y; de Vicente E; Vidal-Vanaclocha F. Prometastatic gene expression patterns in the liver of patients with and without colorectal cancer: pathogenic implications and clinical correlations. Hepatology (in preparation).

Solaun M S, Mendoza L, de Luca M, Gutierrez V, López M-P, Olaso E, B, Sim B K L, Vidal-Vanaclocha F. Endostatin Inhibits Murine Colon Carcinoma Sinusoidal-Type Metastases by Preferential Targeting of Hepatic Sinusoidal Endothelium. Hepatology 35: 1104-1116 (2002).

Valcárcel M, Carrascal T, Crende O, Vidal-Vanaclocha F. IL-18 Regulates Melanoma VLA-4 Integrin Activation through a Hierarchized Sequence of Inflammatory Factors. J Invest Dermatol. 2014 Feb.; 134(2):470-80.

Vidal-Vanaclocha F, Fantuzzi G, Mendoza L, Fuentes A M, Anasagasti M J, Martin J J, Carrascal T, Walsh P, Reznikov L L, Kim S-H, Novick D, Rubinstein M, and Dinarello C A. IL-18 regulates IL-1beta-dependent hepatic melanoma metastasis via vascular cell adhesion molecule-1. Proc Nat Acad Sci USA 97: 734-39 (2000).

Vidal-Vanaclocha F, Mendoza L, Telleria N, Salado C, Valcarcel M, Gallot N, Carrascal T, Egilegor E, Beaskoetxea J, Dinarello. Clinical and experimental approaches to the pathophysiology of interleukin-18 in cancer progression. Cancer Metastasis Rev 25:417-34 (2006).

Vidal-Vanaclocha F. Architectural and Functional Aspects of the Liver with Implications for Cancer Metastasis. P. Bradt (ed.), Liver Metastasis: Biology and Clinical Management, Cancer Metastasis Biology and Treatment 16, DOI 10.1007/978-94-007-0292-9_2, Springer Science+Business Media B.V. 2011a.

Vidal-Vanaclocha F. Regulation of Liver Metastasis-Related Genes at Primary and Metastatic Tumors in the Pathophysiological Context of the Colorectal Cancer Disease. Gut (review article in preparation).

Vidal-Vanaclocha F. The Liver Prometastatic Reaction of Cancer Patients: Implications for Microenvironment-Dependent Colon Cancer Gene Regulation. CAMI 2011;4(2): 163-80.

Vidal-Vanaclocha F. The prometastatic microenvironment of the liver. Cancer Microenvir, 2008; 1: 113-129.

Vidal-Vanaclocha F. The Tumor Microenvironment at Different Stages of Hepatic Metastasis P. Brodt (ed.), Liver Metastasis: Biology and Clinical Management, Cancer Metastasis Biology and Treatment 16, DOI 10.1007/978-94-007-0292-9_3, C_Springer Science+Business Media B. V. 2011b.

Yahagi M, Okabayashi K, Hasegawa H, Tsuruta M, Kitagawa Y. The Worse Prognosis of Right-Sided Compared with Left-Sided Colon Cancers: a Systematic Review and Meta-analysis. J Gastrointest Surg. 2016 Mar;20(3):648-55.

Zhao X, Li L, Starr T K, Subramanian S. Tumor location impacts immune response in mouse models of colon cancer. Oncotarget. 2017 Jun. 9;8(33):54775-54787.

The invention claimed is:

1. An in vitro method of screening an agent potentially capable of modulating onset or progression of hepatic metastasis through inhibition or suppression of selected group 1 genes associated with prometastatic reaction in hepatic tissue, said selected group 1 genes comprising a combination of a majority of genes selected from the group (PRDX4, CRP, ID1, MT1E, TNFSF14, MRC1, ICAM1, IL18, IL10, TNF), said method comprising:
    (a) preparing a primary mix-culture of hepatic parenchymal and non-parenchymal cells obtained from a target patent,
    (b) exposing said primary mix-culture of hepatic parenchymal and non-parenchymal cells to colorectal cancer (CRC) cell-derived soluble factors to induce a prometastatic reaction in vitro;
    (c) after said exposing of step (b), generating a set of reference levels indicative of gene expression levels of said selected group 1 genes of said hepatic parenchymal and non-parenchymal cells of said primary mix culture;
    (d) exposing said primary mix-culture of hepatic parenchymal and non-parenchymal cells to the agent;

(e) after said exposing step (d), measuring gene expression levels of each of said selected group 1 genes of said hepatic parenchymal and non-parenchymal cells of said mix culture that were exposed to said agent, and (f) respectively comparing measured gene expression levels of each of said selected group 1 genes exposed to said agent to corresponding reference levels generated in step (c) whereby to determine if the agent has a positive effect on inhibiting or suppressing activity of group 1 genes associated with metastatic reaction.

2. The method of claim 1, wherein said hepatic parenchymal cells of the primary mix culture comprise hepatocytes and the non-parenchymal cells comprise sinusoidal and non-sinusoidal stromal cells from human or mouse livers.

3. The method of claim 1, wherein after said first exposing step (b), validating the method by obtaining a relationship where said selected group 1 genes in said mix culture are relatively overexpressed, selected group 2 genes in said mix culture are relatively underexpressed, and selected group 3 genes in said mix culture are neither overexpressed or underexpressed where selected group 2 genes comprise a majority of genes (NGF, EPHA1, ERBB2IP, SDC1, COL18A1, KNG1, ADH1B, CYP2E1) and selected group 3 genes comprise a majority of genes (HP, VTN, RPS27, RPL23, GAPDH, TXN, VEGFA, CEACAM1, IGF1, TGFB1, DDR2, NOS2, and BMP7).

4. The method of claim 3, wherein said agent comprises one or more of a pharmaceutical cellular and molecular composition, target-oriented natural product or synthetic chemical analog thereof, a small or large molecule drug or organic compound, and a drug conjugate including but not limited to nanoconjugates and/or polymer-based combinations thereof.

5. The invention of claim 1, wherein said colorectal cancer cell-derived soluble factors of step (b) comprise one of human and mouse-derived cells.

6. The invention of claim 3, wherein (i) said hepatic parenchymal and non-parenchymal cells obtained from a target patent with colorectal cancer, (ii) selected group 1 genes comprise all genes (PRDX4, CRP, ID1, MT1E, TNFSF14, MRC1, ICAM1, IL18, IL 10, TNF), (iii) said selected group 2 genes comprise all genes (NGF, EPHA1, ERBB2IP, SDC1, COL18A1, KNG1, ADH1B, CYP2E1), and (iv) selected group 3 genes comprise all genes (HP, VTN, RPS27, RPL23, GAPDH, TXN, VEGFA, CEACAM1, IGF1, TGFB1, DDR2, NOS2, and BMP7).

\* \* \* \* \*